United States Patent [19]

Meier

[11] Patent Number: 5,204,353
[45] Date of Patent: Apr. 20, 1993

[54] 3-BENZYL-3H-1,2,3-TRIAZOLO[4,5-D]PYRIMIDINES, COMPOSITIONS THEREOF, AND METHOD OF TREATING EPILEPSY THEREWITH

[75] Inventor: René Meier, Buus, Switzerland

[73] Assignee: Ciba-Geigy Corporation, Ardsley, N.Y.

[21] Appl. No.: 814,216

[22] Filed: Dec. 20, 1991

Related U.S. Application Data

[63] Continuation of Ser. No. 622,304, Dec. 5, 1990, abandoned, which is a continuation of Ser. No. 376,793, Jul. 7, 1989, abandoned, which is a continuation-in-part of Ser. No. 173,840, Mar. 28, 1988, abandoned.

[30] Foreign Application Priority Data

Apr. 7, 1987 [CH] Switzerland .......................... 1333/87

[51] Int. Cl.$^5$ ................... A61K 31/505; C07D 487/04
[52] U.S. Cl. ..................................... 514/258; 344/254; 344/322; 548/255
[58] Field of Search .......................... 514/258; 544/254

[56] References Cited

U.S. PATENT DOCUMENTS 3,987,160 10/1976 Broughton e al. .................. 514/258

(List continued on next page.)

FOREIGN PATENT DOCUMENTS 853085 4/1976 Belgium .

(List continued on next page.)

OTHER PUBLICATIONS

Albert, A. Jour. Chem. Soc. Perkin I (4) pp. 345–349 (1975).

(List continued on next page.)

Primary Examiner—Donald G. Daus
Attorney, Agent, or Firm—Irving M. Fishman; Karen G. Kaiser

[57] ABSTRACT

The invention relates to 3H-1,2,3-triazolo[4,5-d]pyrimidine derivatives, especially substituted 3-benzyl-3H-1,2,3-triazolo[4,5-d]-pyrimidines of the general formula

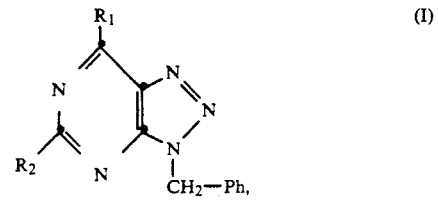

in which Ph represents a phenyl radical substituted by halogen, lower alkyl, trifluoromethyl and/or by cyano, $R_1$ represents a free amino group or an amino group that is substituted aliphatically, cycloaliphatically, cycloaliphatically-aliphatically and/or by acyl, and $R_2$ represents hydrogen, lower alkyl, a free amino group, or an amino group that is substituted aliphatically, cycloaliphaically, cycloaliphatically-aliphatically and/or by acyl, in free form or in form of a salt, with the proviso, that in a compound of formula I in free form, wherein $R_1$ represents N,N-di-$C_1$-$C_6$-alkylamino in which the two N-$C_1$-$C_6$-alkyl groups may be the same or different, N-mono-$C_1$-$C_6$-alkylamino or amino, $R_2$ is other than hydrogen and other than $C_1$-$C_6$-alkyl, if Ph represents a phenyl radical which is monosubstituted by halogen or by trifluoromethyl, and to compounds of formula I in free form wherein either Ph is o-fluorophenyl, $R_1$ is N-mono-methylamino or amino, and $R_2$ is hydrogen or methyl or wherein Ph is o-fluorophenyl, o-chlorophenyl or m-trifluoromethylphenyl, $R_1$ is N,N-dimethylamino, and $R_2$ is hydrogen or wherein Ph is m-fluorophenyl, p-fluorophenyl, o-chlorophenyl, o-trifluoromehylphenyl, m-trifluoromethylphenyl or p-trifluoromethylphenyl, $R_1$ is N-mono-methylamino, and $R_2$ is hydrogen. These compounds and salts can be used as pharmaceutical active ingredients and can be produced in a manner known per se.

2 Claims, No Drawings

U.S. PATENT DOCUMENTS

| | | | |
|---|---|---|---|
| 4,076,711 | 2/1978 | Ganguly et al. | 544/280 |
| 4,157,443 | 6/1979 | Fletcher | 544/254 |
| 4,229,453 | 10/1980 | Roth | 544/280 |
| 4,543,255 | 9/1985 | Shealy | 544/254 |
| 5,034,393 | 7/1991 | Hackler et al. | 514/258 |

FOREIGN PATENT DOCUMENTS

| | | | |
|---|---|---|---|
| 853086 | 4/1976 | Belgium | |
| 450839 | 8/1948 | Canada | 544/254 |
| 157637 | 10/1985 | European Pat. Off. | |
| 272226 | 6/1988 | European Pat. Off. | 544/254 |
| 0288431 | 10/1988 | European Pat. Off. | 544/254 |
| 0062593 | 4/1984 | Japan | 544/254 |
| 59-62595 | 4/1984 | Japan | 544/254 |

OTHER PUBLICATIONS

Burger, A. *MediCinal Chemistry* 20th Ed. Interscience, N.Y., p. 43 (1960).

Nielsen et al., Liebigs Ann. Chem. 1984 pp. 1848–1859 (1984).

Kelley et al., J. Heterocyclic Chem. vol. 23, pp. 1189–1193 (1986).

Kelley et al., J. Med. Chem. vol. 29, pp. 1133–1134 (1986).

Kelley et al. J. Med. Chem. 31, 1005 (1988).

Kelley et al., J. Med. Chem. 31, 2001 (1988).

Kelley et al., J. Med. Chem. 32, 218 (1989).

3-BENZYL-3H-1,2,3-TRIAZOLO[4,5-D]PYRIMIDINES, COMPOSITIONS THEREOF, AND METHOD OF TREATING EPILEPSY THEREWITH

This application is a continuation of application Ser. No. 622,304, filed Dec. 5, 1990 now abandoned, which is a continuation, of application Ser. No. 376,793, filed Jul. 7, 1989 now abandoned, which is a continuation-in-part of application Ser. No. 173,840, filed Mar. 28, 1988 now abandoned.

The invention relates to 3H-1,2,3-triazolo [4,5-d]pyrimidine derivatives, especially substituted 3-benzyl-3H-1,2,3-triazolo[4,5-d]pyrimidines of the general formula

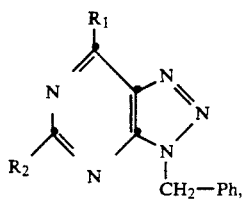

in which Ph represents a phenyl radical substituted by halogen, lower alkyl, trifluoromethyl and/or by cyano, $R_1$ represents a free amino group or an amino group that is substituted aliphatically, cycloaliphatically, cycloaliphatically-aliphatically and/or by acyl, and $R_2$ represents hydrogen, lower alkyl, a free amino group, or an amino group that is substituted aliphatically, cycloaliphatically, cycloaliphatically-aliphatically and/or by acyl, in free form or in form of a salt, with the proviso, that in a compound of formula I in free form, wherein $R_1$ represents N,N-di-$C_1$-$C_6$-alkylamino in which the two N-$C_1$-$C_6$-alkyl groups may be the same or different, N-mono-$C_1$-$C_6$-alkylamino or amino, $R_2$ is other than hydrogen and other than $C_1$-$C_6$-alkyl, if Ph represents a phenyl radical which is monosubstituted by halogen or by trifluoromethyl, and to compounds of formula I in free form wherein either Ph is o-fluorophenyl, $R_1$ is N-mono-methylamino or amino, and $R_2$ is hydrogen or methyl or wherein Ph is o-fluorophenyl, o-chlorophenyl or m-trifluoromethylphenyl, $R_1$ is N,N-di-methylamino, and $R_2$ is hydrogen or wherein Ph is m-fluorophenyl, p-fluorophenyl, o-chlorophenyl, o-trifluoromethylphenyl, m-trifluoromethylphenyl or p-trifluoromethylphenyl, $R_1$ is N-mono-methylamino, and $R_2$ is hydrogen, to processes for the manufacture of such compounds and salts, to pharmaceutical preparations containing them, and to their use as active ingredients in medicaments.

The phenyl radical Ph may have up to and including 3, but preferably 1 or 2, of the mentioned substituents and where it is polysubstituted the substituents may be the same or different. Each of the substituents is bonded preferably in an ortho-position or, less preferably, in a meta-position, but may also be bonded in a para-position. The following may be mentioned as examples: o- and m- and also p-halophenyl, 2,6-dihalophenyl, also 2,3- and 2,5-dihalophenyl as well as 2,3,6- and 2,5,6-trihalophenyl, o-lower alkylphenyl, also m- and p-lower alkylphenyl, m-trifluoromethylphenyl, also o- and p-trifluoromethylphenyl, and o- and m-cyanophenyl, and also p-cyanophenyl.

The phenyl radical Ph may have, for example, up to and including 3, preferably 1 or 2, halogen substituents, each of which is bonded preferably in an ortho-position or, less preferably, in a meta-position. The following may be mentioned as examples: o-halophenyl and 2,6-dihalophenyl, and also 2,3 and 2,5-dihalophenyl as well as 2,3,6- and 2,5,6-trihalophenyl.

Amino groups $R_1$ and $R_2$ that are substituted aliphatically, cycloaliphatically, cycloaliphatically-aliphatically and/or by acyl are, for example, amino groups monosubstituted by an aliphatic, cycloaliphatic or cycloaliphatic-aliphatic radical or by acyl, or amino groups disubstituted by aliphatic, cycloaliphatic or cycloaliphatic-aliphatic radicals, or by an aliphatic radical as well as a cycloaliphatic radical or acyl. Suitable aliphatic radicals are, for example: lower alkyl, lower alkoxy-lower alkyl and hydroxy-lower alkyl; a suitable cycloaliphatic radical is, for example, cycloalkyl; a suitable cycloaliphatic-aliphatic radical is, for example, cycloalkyl-lower alkyl, and a suitable acyl radical is, for example, lower alkanoyl. The following may be mentioned as examples of radicals $R_1$ and $R_2$: amino, N-mono and N,N-di-lower alkylamino, N-(lower alkoxy-lower alkyl)amino, N-(hydroxy-lower alkyl)amino, N-(hydroxy-lower alkyl)-N-lower alkylamino, N-mono- and N,N-di-cycloalkylamino, N-cycloalkyl-N-lower alkylamino, N-mono- and N,N-di-(cycloalkyl-lower alkyl)amino, N-(cycloalkyl-lower alkyl)-N-lower alkylamino, N-lower alkanoylamino and N-lower alkanoyl-N-lower alkylamino.

The invention relates, for example, to compounds of the general formula I in which, in consideration of the proviso mentioned hereinbefore, Ph represents a phenyl radical that is substituted by at least one halogen atom, $R_1$ represents a free amino group or an amino group that is substituted aliphatically, cycloaliphatically, cycloaliphatically-aliphatically and/or by acyl, and $R_2$ represents hydrogen, lower alkyl, a free amino group, or an amino group that is substituted aliphatically, cycloaliphatically, cycloaliphatically-aliphatically and/or by acyl, in free form or in form of a salt, and to compounds of formula I in free form wherein either Ph is o-fluorophenyl, $R_1$ is N-mono-methylamino or amino, and $R_2$ is hydrogen or methyl or wherein Ph is o-fluorophenyl or o-chlorophenyl, $R_1$ is N,N-di-methylamino, and $R_2$ is hydrogen or wherein Ph is m-fluorophenyl, p-fluorophenyl or o-chlorophenyl, $R_1$ is N-mono-methylamino, and $R_2$ is hydrogen, to processes for the manufacture of such compounds and salts, to pharmaceutical preparations containing them and to the use thereof as active ingredients in medicaments.

Hereinbefore and hereinafter, unless defined otherwise, organic groups and compounds referred to as "lower" preferably contain up to and including 7, especially up to and including 4, carbon atoms (C-atoms).

Halogen is, for example, halogen having an atomic number of up to and including 35, such as fluorine, chlorine or, less preferably, bromine.

Lower alkyl is, for example, $C_1$-$C_4$-alkyl, such as methyl, ethyl, n-propyl, isopropyl or n-butyl, or also secondary butyl, isobutyl or tertiary butyl, but it can also be a $C_5$-$C_7$-alkyl group, i.e. a pentyl, hexyl or heptyl group.

N-mono-lower alkylamino is, for example, N-$C_1$-$C_7$-alkylamino, especially N-$C_1$-$C_4$-alkylamino, such as N-methylamino or N-ethylamino.

N,N-di-lower alkylamino is, for example, N,N-di-$C_1$-$C_7$-alkylamino, especially N,N-di-$C_1$-$C_4$-alkylamino, in each of which the two N-alkyl groups may be the same or different, such as N,N-dimethyl-, N,N-diethyl-, N,N-diisopropyl- or N-butyl-N-methylamino.

N-(lower alkoxy-lower alkyl)amino is, for example, N-($C_1$–$C_4$-alkoxy-, such as methoxy- or ethoxy-, $C_1$–$C_7$-alkyl)amino, especially N-($C_1$–$C_4$-alkoxy-, such as methoxy- or ethoxy-, $C_1$–$C_4$-alkyl)amino, such as N-(methoxymethyl)amino or N-(1-methoxyethyl)amino.

N-(hydroxy-lower alkyl)amino is, for example, N-(hydroxy-$C_1$–$C_7$-alkyl)-amino, especially N-(hydroxy-$C_1$–$C_4$-alkyl)-amino, such as N-(hydroxymethyl)amino. or N-(1-hydroxyethyl)amino.

N-(hydroxy-lower alkyl)-N-lower alkylamino is, for example, N-(hydroxy-$C_1$–$C_7$-alkyl)-N-$C_1$–$C_7$-alkylamino, especially N-(hydroxy-$C_1$–$C_4$-alkyl)-N-$C_1$–$C_4$-alkylamino, such as N-(1-hydroxyethyl)-N-methylamino or N-(hydroxymethyl)-N-ethylamino.

N-monocycloalkylamino is, for example, N-$C_3$–$C_8$-cycloalkylamino, especially N-$C_3$–$C_6$-cycloalkylamino, such as N-cyclopropylamino or N-cyclohexylamino.

N,N-dicycloalkylamino is, for example, N,N-di-$C_3$–$C_8$-cycloalkylamino, especially N,N-di-$C_3$–$C_6$-cycloalkylamino, in each of which the two N-cycloalkyl groups may be the same or different, such as N,N-dicyclohexylamino or N-cyclohexyl-N-cyclopropylamino.

N-cycloalkyl-N-lower alkylamino is, for example, N-$C_3$–$C_8$-cycloalkyl-N-$C_1$–$C_7$-alkylamino, especially N-$C_3$–$C_6$-cycloalkyl-N-$C_1$–$C_4$-alkylamino, such as N-cyclopropyl-N-methylamino or N-cyclohexyl-N-ethylamino.

N-mono(cycloalkyl-lower alkyl)amino is, for example, N-($C_3$–$C_8$-cycloalkyl-$C_1$–$C_7$-alkyl)amino, especially N-($C_3$–$C_6$-cycloalkyl-$C_1$–$C_4$-alkyl)-amino, such as N-(cyclopropylmethyl)amino or N-(1-cyclohexylethyl)amino.

N,N-di(cycloalkyl-lower alkyl)amino is, for example, N,N-di($C_3$–$C_8$-cycloalkyl-$C_1$–$C_7$-alkyl)amino, especially N,N-di($C_3$–$C_6$-cycloalkyl-$C_1$–$C_4$-alkyl)amino, in each of which the two N-(cycloalkylalkyl) groups may be the same or different, such as N,N-di(cyclopropylmethyl)amino or N-(cyclopropylmethyl)-N-(1-cyclohexylethyl)amino.

N-(cycloalkyl-lower alkyl)-N-lower alkylamino is, for example, N-($C_3$–$C_8$-cycloalkyl-$C_1$–$C_7$-alkyl)-N-$C_1$–$C_7$-alkylamino, especially N-($C_3$–$C_6$-cycloalkyl-$C_1$–$C_4$-alkyl)-N-$C_1$–$C_4$-alkylamino, such as N-(cyclopropylmethyl)-N-ethylamino or N-(1-cyclohexylethyl)-N-methylamino.

Lower alkanoyl is, for example, $C_2$–$C_5$-alkanoyl, such as acetyl, propionyl, butyryl, isobutyryl or pivaloyl.

N-lower alkanoylamino is, for example, N-$C_2$–$C_5$-alkanoylamino, such as N-acetyl-, N-propionyl-, N-butyryl- or N-pivaloyl-amino.

N-lower alkanoyl-N-lower alkylamino is, for example, N-$C_2$–$C_5$-alkanoyl-N-$C_1$–$C_7$-alkylamino, especially N-$C_2$–$C_5$-alkanoyl-N-$C_1$–$C_4$-alkylamino, such as N-acetyl-N-propylamino or N-butyryl-N-methylamino.

The compounds I are able to form salts by way of their basic centres. Salts of compounds I are therefore especially corresponding acid addition salts, preferably pharmaceutically acceptable acid addition salts. These are formed, for example, with strong inorganic protonic acids, such as mineral acids, for example sulphuric acid, a phosphoric acid or a hydrohalic acid, with strong organic carboxylic acids, such as lower alkanecarboxylic acids, for example acetic acid, optionally unsaturated dicarboxylic acids, for example malonic, maleic or fumaric acid, or hydroxycarboxylic acids, for example tartaric or citric acid, or with sulphonic acids, such as lower alkanesulphonic or optionally substituted benzenesulphonic acids, for example methanesulphonic or p-toluene-sulphonic acid.

Also included are salts that are unsuitable for pharmaceutical uses, since these can be used, for example, for the isolation or purification of free compounds I and the pharmaceutically acceptable salts thereof.

The compounds I and the pharmaceutically acceptable salts thereof have valuable pharmacological properties, especially a pronounced anticonvulsive activity, which may be demonstrated, for example, by way of a marked metrazole antagonism when administered to mice in a dosage range of from approximately 10 mg/kg p.o., and by way of a pronounced protective action against convulssions induced by electric shock when administered to mice and rats in a dosage range of from approximately 3 mg/kg p.o.

The compounds I and the pharmaceutically acceptable salts thereof are accordingly especially suitable for the treatment of convulsions of various origins, for example for the treatment of epilepsy. They can accordingly be used as anticonvulsive, for example anti-epileptic, active ingredients in medicaments. The industrial production of the active substances may also be included.

The invention relates in the first place to compounds of formula I in which, in consideration of the proviso mentioned hereinbefore, Ph represents a phenyl radical substituted by halogen, lower alkyl, trifluoromethyl and/or by cyano, $R_1$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino or N-lower alkanoyl-N-lower alkylamino, and $R_2$ represents hydrogen, lower alkyl, amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-dicycloalkylamino, N-cycloalkyl-N-lower alkylamino, N-mono- or N,N-di(cycloalkyl-lower alkyl)amino, N-(cycloalkyl-lower alkyl)-N-lower alkylamino, N-lower alkanoylamino or N-lower alkanoyl-N-lower alkylamino, in free form or in form of a salt, and to compounds of formula I in free form wherein either Ph is o-fluorophenyl, $R_1$ is N-monomethylamino or amino, and $R_2$ is hydrogen or methyl or wherein Ph is o-fluorophenyl, o-chlorophenyl or m-trifluoromethylphenyl, $R_1$ is N,N-di-methylamino, and $R_2$ is hydrogen or wherein Ph is m-fluorophenyl, p-fluorophenyl, o-chlorophenyl, o-trifluoromethylphenyl, m-trifluoromethylphenyl or p-trifluoromethylphenyl, $R_1$ is N-mono-methylamino, and $R_2$ is hydrogen.

The invention relates especially to compounds of formula I in which, in consideration of the proviso mentioned hereinbefore, Ph represents a phenyl radical that is substituted by at least one halogen atom, $R_1$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino or N-lower alkanoyl-N-lower alkylamino and $R_2$ represents hydrogen, lower alkyl, amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino or N-lower alkanoyl-N-lower alkylamino, in free form or in form of a salt, and to compounds of formula I in free form wherein either Ph is o-fluorophenyl, $R_1$ is N-mono-methylamino or amino, and $R_2$ is hydrogen or methyl or wherein Ph is o-fluorophenyl or o-chlorophenyl, $R_1$ is N,N-dimethylamino, and $R_2$ is hydrogen or wherein Ph is m-fluorophenyl, p-fluorophenyl or o-chlorophenyl, $R_1$ is N-mono-methylamino, and $R_2$ is hydrogen.

The invention relates especially to compounds of formula I in which, in consideration of the proviso mentioned hereinbefore, Ph represents 2-, 3- or 4-halophenyl, such as 2-fluoro-, 3-fluoro-, 4-fluoro- or 2-chlorophenyl, 2,3-, 2,5- or 2,6-dihalophenyl, such as 2,3-, 2,5- or 2,6-difluorophenyl, or 6-chloro-2-fluorophenyl, 2-, 3- or 4-$C_1$-$C_4$-alkylphenyl, such as 2-methylphenyl, 2-, 3- or 4-trifluoromethylphenyl or 2-, 3- or 4-cyanophenyl, wherein halogen may in each case be halogen having an atomic number of up to and including 35, $R_1$ represents amino, N-$C_1$-$C_4$-alkylamino, such as N-methylamino or N-ethylamino, N,N-di-$C_1$-$C_4$-alkylamino, such as N,N-dimethylamino, N,N-diethylamino or N-butyl-N-methylamino, N-$C_3$-$C_6$-cycloalkylamino, such as N-cyclopropylamino or N-cyclohexylamino, or N-lower alkanoylamino, such as N-acetylamino, and $R_2$ represents hydrogen, $C_1$-$C_4$-alkyl, such as methyl or ethyl, amino, N-$C_1$-$C_4$-alkylamino, such as N-methylamino or N-ethylamino, N,N-di-$C_1$-$C_4$-alkylamino, such as N,N-dimethylamino, N,N-diethylamino or N-butyl-N-methylamino, N-$C_3$-$C_6$-cycloalkylamino, such as N-cyclopropylamino or N-cyclohexylamino, or N-lower alkanoylamino, such as N-acetylamino, in free form or in form of a salt, and to compounds of formula I in free form wherein either Ph is o-fluorophenyl, $R_1$ is N-mono-methylamino or amino, and $R_2$ is hydrogen or methyl or wherein Ph is o-fluorophenyl, o-chlorophenyl or m-trifluoromethylphenyl, $R_1$ is N,N-di-methylamino, and $R_2$ is hydrogen or wherein Ph is m-fluorophenyl, p-fluorophenyl, o-chlorophenyl, o-trifluoromethylphenyl, m-trifluoromethylphenyl or p-trifluoromethylphenyl, $R_1$ is N-mono-methylamino, and $R_2$ is hydrogen.

The invention relates especially to compounds of formula I in which, in consideration of the proviso mentioned hereinbefore, Ph represents 2-halophenyl that may in addition be substituted in the 3-, 5- or 6-position by halogen having an atomic number of up to and including 35, such as fluorine or chlorine, such as 2-chloro- or 2-fluoro-phenyl, 2,3-, 2,5- or 2,6-difluorophenyl or 6-chloro-2-fluorophenyl, $R_1$ represents amino, N-$C_1$-$C_4$-alkylamino, such as N-methylamino or N-ethylamino, N,N-di-$C_1$-$C_4$-alkylamino, such as N,N-dimethylamino, N,N-diethylamino or N-butyl-N-methylamino, N-$C_3$-$C_6$-cycloalkylamino, such as N-cyclopropylamino or N-cyclohexylamino, or N-lower alkanoylamino, such as N-acetylamino, and $R_2$ represents hydrogen, $C_1$-$C_4$-alkyl, such as methyl or ethyl, amino, N-$C_1$-$C_4$-alkylamino, such as N-methylamino or N-ethylamino, N,N-di-$C_1$-$C_4$-alkylamino, such as N,N-dimethylamino, N,N-diethylamino or N-butyl-N-methylamino, N-$C_3$-$C_6$-cycloalkylamino, such as N-cyclopropylamino or N-cyclohexylamino, or N-lower alkanoylamino, such as N-acetylamino, in free form or in form of a salt, and to compounds of formula I in free form wherein either Ph is o-fluorophenyl, $R_1$ is N-mono-methylamino or amino, and $R_2$ is hydrogen or methyl or wherein Ph is o-fluorophenyl or o-chlorophenyl, $R_1$ is N,N-di-methylamino, and $R_2$ is hydrogen or wherein Ph is o-chlorophenyl, $R_1$ is N-mono-methylamino, and $R_2$ is hydrogen.

The invention relates more especially to compounds of formula I in which, in consideration of the proviso mentioned hereinbefore, Ph represents 2- or 3-fluorophenyl, 2-chlorophenyl, 2,6-difluorophenyl or 2-$C_1$-$C_4$-alkylphenyl, such as 2-methylphenyl, $R_1$ represents N-$C_1$-$C_4$-alkylamino, such as N-methylamino or N-ethylamino, N,N-di-$C_1$-$C_4$-alkylamino, such as N,N-dimethylamino, N,N-diethylamino or N-butyl-N-methylamino, or N-$C_3$-$C_6$-cycloalkylamino, such as N-cyclopropylamino or N-cyclohexylamino, and $R_2$ represents hydrogen, $C_1$-$C_4$-alkyl, such as methyl or ethyl, or amino, in free form or in form of a salt, and to compounds of formula I in free form wherein either Ph is o-fluorophenyl, $R_1$ is N-mono-methylamino, and $R_2$ is hydrogen or methyl or wherein Ph is o-fluorophenyl or o-chlorophenyl, $R_1$ is N,N-di-methylamino, and $R_2$ is hydrogen or wherein Ph is m-fluorophenyl or o-chlorophenyl, $R_1$ is N-mono-methylamino, and $R_2$ is hydrogen.

The invention relates especially to compounds of formula I in which, in consideration of the proviso mentioned hereinbefore, Ph represents 2-fluorophenyl which may in addition be substituted in the 5- or 6-position by halogen having an atomic number of up to and including 35, such as fluorine or chlorine, such as 2-fluorophenyl, 2,5-or 2,6-difluorophenyl or 6-chloro-2-fluorophenyl, $R_1$ represents amino, N-$C_1$-$C_4$-alkylamino, such as N-methylamino or N-ethylamino, N,N-di-$C_1$-$C_4$-alkylamino, such as N,N-dimethylamino, N,N-diethylamino or N-butyl-N-methylamino, or N-$C_3$-$C_6$-cycloalkylamino, such as N-cyclopropylamino or N-cyclohexylamino, and $R_2$ represents hydrogen, $C_1$-$C_4$-alkyl, such as methyl or ethyl, or amino, in free form or in form of a salt, and to compounds of formula I in free form wherein either Ph is o-fluorophenyl, $R_1$ is N-mono-methylamino or amino, and $R_2$ is hydrogen or methyl or wherein Ph is o-fluorophenyl, $R_1$ is N,N-di-methylamino, and $R_2$ is hydrogen.

The invention relates more especially to compounds of formula I in which, in consideration of the proviso mentioned hereinbefore, Ph represents 2-fluorophenyl or 2,6-difluorophenyl, $R_1$ represents amino, N-$C_1$-$C_4$-alkylamino, such as N-methylamino, or N,N-di-$C_1$-$C_4$-alkylamino, such as N,N-dimethylamino, and $R_2$ represents hydrogen or $C_1$-$C_4$-alkyl, such as methyl, in free form or in form of a salt, and to compounds of formula I in free form wherein either Ph is o-fluorophenyl, $R_1$ is N-mono-methylamino or amino, and $R_2$ is hydrogen or methyl or wherein Ph is o-fluorophenyl, $R_1$ is N,N-di-methylamino, and $R_2$ is hydrogen.

The invention relates most especially to compounds of formula I in which, in consideration of the proviso mentioned hereinbefore, Ph represents 2-fluorophenyl, $R_1$ represents N-$C_1$-$C_4$-alkylamino, such as N-methylamino, or N,N-di-$C_1$-$C_4$-alkylamino, such as N,N-dimethylamino, and $R_2$ represents hydrogen or amino, in free form or in form of a salt, and to compounds of formula I in free form wherein either Ph is o-fluorophenyl, $R_1$ is N-monomethylamino, and $R_2$ is hydrogen or wherein Ph is o-fluorophenyl, $R_1$ is N,N-di-methylamino, and $R_2$ is hydrogen.

The invention relates specifically to the compounds of formula I mentioned in the Examples and the salts thereof.

The invention also relates to a process for the manufacture of compounds I and the salts thereof which is based on techniques that are known per se and is characterised in that a) in a compound of formula

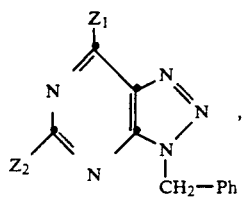

in which $Z_1$ represents a nucleofugal leaving group $X_1$ and $Z_2$ represents a nucleofugal leaving group $X_2$ or a radical $R_2$, or in which $Z_1$ is a radical $R_1$ and $Z_2$ represents a nucleofugal leaving group $X_2$, or in a tautomer and/or salt thereof, $X_1$ is converted into $R_1$ and/or $X_2$ is converted into $R_2$, or b) the compound Y-H is eliminated from a compound of formula

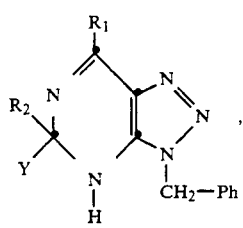

in which Y represents hydroxy, mercapto, optionally aliphatically substituted amino, or anilino, or from a tautomer and/or salt thereof, or c) for the manufacture of a compound I, in which $R_2$ represents amino, or a salt thereof, a compound of formula

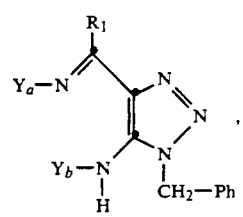

in which one of the radicals $Y_a$ and $Y_b$ represents cyano and the other represents hydrogen, or a tautomer and-/or a salt thereof, is cyclised, or d) a salt of formula

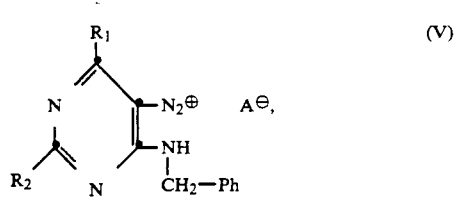

in which A represents the anion of a protonic acid, is cyclised, or e) a compound of formula

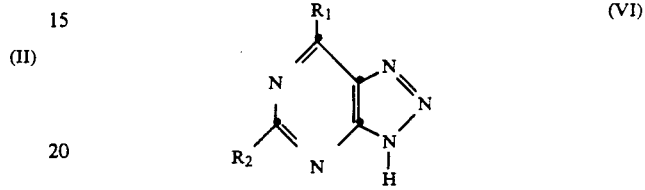

or a salt thereof is reacted with a compound of formula $X_1$—$CH_2$—Ph (VII), in which $X_1$ represents a nucleofugal leaving group, and, if desired, in each case an isomeric mixture that may be obtained in accordance with the process is separated into the components and the isomer of formula I is isolated, a compound I obtained according to the process or by another method is converted into a different compound I, a free compound I obtained according to the process is converted into a salt or a salt of a compound I obtained according to the process is converted into the free compound I or into a different salt of compound I, and/or a stereoisomeric mixture that may be obtained according to the process is separated into the stereoisomers and the desired stereoisomer is isolated.

The reactions of the process that are described hereinbefore and hereinafter, and also the manufacture of novel starting materials and intermediates, are carried out in a manner known per se. Even if this is not expressly mentioned, the reactions are carried out, analogously to the methods of reaction and formation of known starting materials and intermediates, under the reaction conditions customary in each case, for example as required with cooling, at room temperature or with heating, for example in a temperature range of from approximately −10° C. to approximately +250° C., preferably from approximately 20° C. to approximately 200° C., with the use of the auxiliary agents that are customary in each case, such as catalysts, condensing agents and solvolysis agents, in the absence or, customarily, in the presence of a suitable solvent or diluent or a mixture thereof, optionally in a closed vessel, in an inert gas atmosphere and/or under anhydrous conditions.

Each of the starting materials of formulae II, III, IV, V, VI and VII listed hereinbefore and hereinafter that are used for the manufacture of compounds I and the salts thereof is either known or can be produced by methods that are known per se. Starting materials with basic centres may be in the form of salts, such as acid addition salts, for example with the acids listed hereinbefore.

Salts of compounds II, III or IV or, where applicable, their respective tautomers, are especially acid addition salts, preferably with strong inorganic or organic acids, for example analogous to the kind mentioned hereinbefore for acid addition salts of compounds I.

Tautomers of starting compounds II used in process variant a), or salts thereof, may occur, for example, when in compounds II or salts thereof the groups $Z_1$ and/or $Z_2$ represent hydroxy or mercapto and/or one of the groups $Z_1$ and $Z_2$ represents optionally mono-substituted amino. Accordingly, for example, compounds II or salts thereof having enol, enthiol and/or enamine partial structures may also be in protomeric form, that is to say in the form of corresponding oxo, thioxo and/or imino tautomers, and/or may be in dynamic equilibrium with the latter.

Nucleofugal leaving groups $X_1$ and $X_2$ in compounds II are, for example, optionally etherified or esterified hydroxy or mercapto groups, sulphinyl and sulphonyl groups, or sulphonium groups. Etherified hydroxy is, for example, lower alkoxy, such as methoxy, or optionally substituted phenyl-lower alkoxy, such as optionally substituted benzyloxy. Esterified hydroxy is especially hydroxy esterified by a mineral acid or an organic sulphonic acid, especially halogen, such as chlorine, bromine or iodine, sulphonyloxy, such as optionally halosubstituted lower alkanesulphonyloxy, for example methanesulphonyloxy or trifluoromethanesulphonyloxy, cycloalkanesulphonyloxy, for example cyclohexanesulphonyloxy, or benzenesulphonyloxy optionally substituted by lower alkyl or by halogen, for example benzenesulphonyloxy, p-bromophenylsulphonyloxy or p-toluenesulphonyloxy, or lower alkanoyloxy, for example acetoxy. Etherified mercapto is, for example, lower alkylthio, such as methylthio, optionally substituted arylthio, such as optionally substituted phenyl-thio or naphthylthio, for example phenylthio, p-tolylthio or naphthylthio, or optionally substituted aryl-lower alkyl-thio, such as optionally substituted benzyl- or naphthylmethylthio, for example benzylmethylthio, p-bromobenzylmethylthio or naphthylmethylthio. Esterified mercapto groups are, for example, lower alkanoylthio groups, such as acetylthio. Sulphinyl groups are, for example, lower alkanesulphinyl groups, such as methanesulphinyl, optionally substituted arylsulphinyl groups, such as optionally substituted benzene- or naphthyl-sulphinyl, for example p-toluene- or naphthylsulphinyl, or optionally substituted benzylsulphinyl, such as benzyl- or p-chlorobenzyl-sulphinyl. Sulphonyl groups are, for example, lower alkanesulphonyl groups, such as methanesulphonyl, optionally substituted arylsulphonyl groups, such as optionally substituted benzene- or naphthyl-sulphonyl, for example benzene- or naphthyl-sulphonyl, or optionally substituted benzylsulphonyl, such as benzyl- or p-methylbenzyl-sulphonyl. Sulphonium groups are, for example, di-lower alkylsulphonium groups, such as dimethylsulphonium.

The conversion of $X_1$ and/or $X_2$ in compounds II, tautomers thereof and their respective salts into radicals $R_1$ and/or $R_2$ is carried out by reaction with compounds of formula $H-R_1$ (IIb) and/or $H-R_2$ (IIj), or a salt of either, with the removal of compounds $X_1$-H and/or $X_2$-H.

The reaction of compounds II, tautomers thereof and their respective salts with compounds IIb and/or IIj or their respective salts is carried out in customary manner, for example while cooling, at room temperature or while heating, for example in a temperature range of from approximately $-20°$ to approximately $+250°$ C., preferably from approximately $-10°$ to approximately $+200°$ C., optionally in the presence of an inert solvent or diluent or a mixture thereof, optionally in the presence of a waterbinding agent, optionally in the presence of a basic agent and/or under an inert gas, such as nitrogen.

Suitable inert solvents or diluents are, for example, water, cyclic ethers, aromatic hydrocarbons, N,N-di-lower alkyl-lower alkanoic acid amides, phosphoric acid lower alkylamides, di-lower alkyl sulphoxides, cyclic amines and, especially, optionally in the form of mixtures with water, lower alkanols, such as tetrahydrofuran, dioxan, benzene, toluene, xylene, N,N-dimethylformamide, hexamethylphosphoric acid triamide, dimethyl sulphoxide, N-methylmorpholine and, especially, optionally in the form of mixtures with water, methanol and ethanol. It is also possible for the manufacture of compounds I in which at least one of the radicals $R_1$ and $R_2$ represents an amino group substituted as indicated, or salts thereof, for corresponding amines $H-R_1$ (IIb; $R_1$=amino substituted as indicated) and/or $H-R_2$ (IIj; $R_2$=amino substituted as indicated), which at the reaction temperatures can be handled in liquid form, to be used in excess and employed as solvents or diluents and/or cosolvents, optionally also in dissolved form, for example in the form of aqueous solutions.

Water-binding agents are, for example, oxides of phosphorus, such as phosphorus pentoxide, sulphates of alkali metals or alkaline earth metals, such as sodium or calcium sulphate, halides of alkaline earth metals, such as calcium chloride, or carbodiimides, such as N,N'-dicyclohexylcarbodiimide.

Basic agents are, for example, alkali metal or alkaline earth metal hydroxides, hydrides, amides, lower alkanolates, carbonates, di-lower alkyl amides or lower alkylsilyl amides, lower alkylamines, optionally N-lower alkylated cycloalkylamines, basic heterocycles, ammonium hydroxides and also carbocyclic amines. The following examples may be mentioned: sodium hydroxide, hydride, amide and methanolate, potassium tert.-butanolate, potassium carbonate, lithium diisopropylamide, potassium bis(trimethylsilyl)amide, calcium hydride, triethylamine, cyclohexylamine, N-cyclohexyl-N,N-dimethylamine, pyridine, benzyltrimethylammonium hydroxide and 1,5-diazabicyclo[4.5.0]undec-5-ene (DBU). For the manufacture of compounds I in which at least one of the radicals $R_1$ and $R_2$ represents an amino group substituted as indicated, or salts thereof, there may preferably be used instead of an additional basic agent corresponding amines $H-R_1$ (IIb; $R_1$=amino substituted as indicated) and/or $H-R_2$ (IIj; $R_2$=amino substituted as indicated), which in such cases are advantageously employed in excess.

In a preferred form of process variant a) a compound of formula

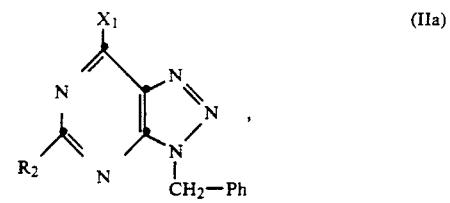

(IIa)

in which $X_1$ represents a nucleofugal leaving group, preferably hydroxy or halogen, such as chlorine or bromine, or a tautomer, for example a corresponding 6H-7-oxo compound, and/or a salt thereof is reacted with ammonia or an amine of formula H-R$_1$ (IIb) or a salt thereof to remove a compound X$_1$-H.

The conversion of X$_1$ in compounds IIa, tautomers thereof and their respective salts into a radical R$_1$ (removal of X$_1$-H) is carried out in customary manner, for example at room temperature or while heating, for example in a temperature range of from approximately 20° to approximately 250° C., preferably from approximately 20° to approximately 200° C., optionally in the presence of an inert solvent or diluent, for example of the kind indicated hereinbefore, or a mixture thereof, optionally in the presence of a basic agent, for example of the kind mentioned hereinbefore, optionally in the presence of a water-binding agent, for example of the kind indicated hereinbefore, and/or under an inert gas, such as nitrogen.

In a further preferred form of process variant a), to produce compounds I in which R$_2$ has a meaning other than hydrogen, or salts thereof, a compound of formula

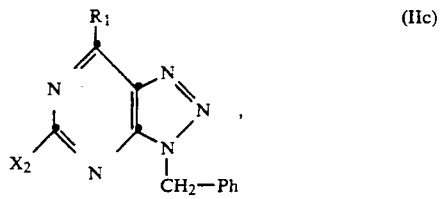
(IIc)

in which X$_2$ represents a nucleofugal leaving group, preferably hydroxy or halogen, such as chlorine or bromine, or a tautomer and/or salt thereof, is reacted with a compound of formula H-R$_2$ (IIj; R$_2\neq$hydrogen), or a salt thereof, to remove a compound X$_2$-H.

The conversion of X$_2$ in compounds IIc, tautomers thereof and their respective salts into a group R$_2$ having a meaning other than hydrogen (removal of X$_2$-H) is carried out in customary manner, for example as described hereinbefore for the conversion of compounds IIa, tautomers thereof and their respective salts into compounds I or salts thereof.

In a further preferred form of process variant a), to manufacture compounds I in which R$_2$ represents hydrogen, or salts thereof, a compound IIc in which X$_2$ represents a nucleofugal leaving group, preferably halogen, such as chlorine or bromine, or a tautomer and/or salt thereof, is reduced.

Suitable reducing agents are, for example, Raney nickel and hydrogen. Reduction with Raney nickel is carried out in customary manner, for example by reacting with a solution of the metal in a lower alkanol, such as methanol, while heating, for example in a temperature range of from approximately 20° to approximately 140° C., preferably from approximately 50° to approximately 100° C. Reduction with hydrogen is advantageously carried out in the presence of a hydrogenation catalyst. Suitable hydrogenation catalysts are, for example, elements of sub-group VIII of the Periodic Table of Elements or derivatives thereof, such as palladium, platinum, platinum oxide, ruthenium, rhodium, a tris(-triphenylphosphane)-rhodium(I) halide, for example chloride, or Raney nickel, the catalyst optionally being applied to a support material, such as active carbon, alkali metal carbonate or sulphate or a silica gel. The catalytic hydrogenation is preferably carried out in a polar solvent or diluent, especially in a lower alkanol, such as methanol, or in a strong inorganic acid, such as a hydrohalic acid, for example hydrochloric acid, or a strong organic carboxylic acid, especially aqueous acetic acid or glacial acetic acid, with cooling or heating, preferably in a temperature range of from approximately $-10°$ to approximately $+120°$ C., especially from approximately 0° to approximately 100° C., especially advantageously at room temperature.

In a further preferred form of process variant a), starting from a compound of formula

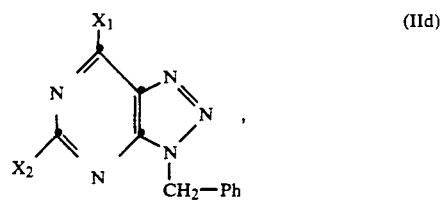
(IId)

in which each of X$_1$ and X$_2$ represents a nucleofugal leaving group of the kind described hereinbefore, preferably hydroxy or halogen, such as chlorine or bromine, or a tautomer and/or salt thereof, in succession the X$_1$ group is replaced by an R$_1$ radical and the X$_2$ group is replaced by an R$_2$ radical. Thus, for example, preferably a compound IId or a tautomer and/or salt thereof may first of all be reacted with ammonia or an amine of formula H-R$_1$ (IIb) or a salt thereof to remove a compound X$_1$-H, and the resulting intermediate IIc or a tautomer and/or salt thereof may then be converted into a compound of formula I in which R$_2$ represents free amino, amino substituted as indicated, or hydrogen, or into a salt thereof, by reaction with ammonia or an amine of formula H-R$_2$ (IIj; R$_2=$free amino or amino substituted as indicated) or a salt thereof to remove a compound X$_2$-H, or by reduction, for example by the action of Raney nickel or by catalytic hydrogenation of the kind described hereinbefore.

The conversion of X$_1$ and X$_2$ in compounds IId, tautomers thereof and their respective salts into R$_1$ and R$_2$, respectively, is carried out in customary manner, for example as described hereinbefore for the corresponding conversion of compounds IIa and IIc, respectively, tautomers thereof and their respective salts into compounds I or salts thereof, and the intermediate IIc which may first be obtained from IId does not need to be isolated but is advantageously further reacted in situ, without additional purification, to form a compound I or a salt thereof.

The compounds IIb and IIj and their respective salts are known. The compounds IIa, IIc and IId, tautomers thereof and their respective salts can be manufactured analogously to known methods, for example by reaction of a compound of formula

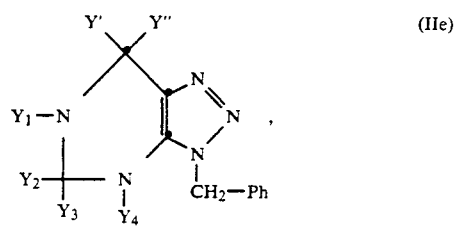
(IIe)

in which either Y' and Y" together represent optionally functionally modified oxo X$_3$, Y$_1$ represents hydrogen and either Y$_2$ represents R$_2$ and Y$_3$ and Y$_4$ together represent an additional bond, or $Y_2$ and $Y_3$ together represent optionally functionally modified oxo $X_3$ and $Y_4$ represents hydrogen, or in which $Y''$ represents $R_1$, $Y'$ and $Y_1$ together represent an additional bond, $Y_2$ and $Y_3$ together represent optionally functionally modified oxo $X_3$, and $Y_4$ represents hydrogen, or a tautomer and/or salt thereof, with a halogenating agent, and optional further reaction, in customary manner, of a resulting compound IIa, IIc or IId in which each of $X_1$ and $X_2$ represents halogen, or of a tautomer and/or salt thereof, with a compound of formula $X_1$-H and/or $X_2$-H in which each of $X_1$ and $X_2$, independently of the other, represents one of the above-described nucleofugal leaving groups other than halogen.

Optionally functionally modified oxo $X_3$ in compounds IIe, tautomers thereof and their respective salts is, for example, thioxo or optionally substituted imino, but preferably oxo. Optionally substituted imino is, for example, a group =N-R', in which R' has the same meaning as in the partial structure —NHR', which represents a radical $R_1$ and/or $R_2$, such as imino, N-lower alkylimino, N-cycloalkylimino or N-lower alkanoylimino.

What has been said hereinbefore concerning salts and/or tautomers of compounds II applies in an analogous manner to salts and/or tautomers of compounds IIe. Thus, especially corresponding keto/enol, thioketo/enthiol and/or imino/enamine tautomers are possible.

Halogenating agents are, for example, halides of phosphorus or sulphur, such as phosphorus trihalides, phosphorus pentahalides, phosphorus oxytrihalides, thionyl halides or sulphuryl halides, for example phosphorus trichloride, phosphorus tribromide, phosphorus pentachloride, phosphorus oxytrichloride, thionyl chloride or sulphuryl chloride, but may also be, for example, acid halides, such as acid chlorides, of carbonic acid, for example phosgene.

The reaction of a compound IIe or a tautomer and/or salt thereof with a halogenating agent is carried out under customary reaction conditions, for example while heating, for example in a temperature range of from approximately 20° to approximately 200° C. and in an inert solvent, such as a halo-lower alkane, for example tetrachloromethane, but preferably using a solution or suspension of compound IIe or a tautomer and/or salt thereof in an excess of the halogenating agent.

Thus, for example, a compound IIa in which $X_1$ is halogen, such as chlorine, or a tautomer and/or salt thereof, is obtained by reacting a compound IIe in which $Y'$ and $Y''$ together represent an $X_3$ group, preferably oxo, Y1 represents hydrogen, $Y_2$ represents an $R_2$ group and $Y_3$ and $Y_4$ together represent an additional bond, or a tautomer and/or salt thereof, with a halogenating agent, for example phosphorus oxytrichloride, it being possible for the corresponding compound IIe or a tautomer and/or salt thereof to be obtained, for example, by reaction of a compound of formula

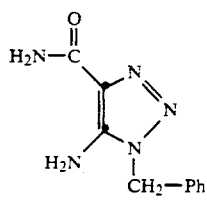

(IIf)

or a salt thereof with a compound of formula $R_2$-X (IIg), in which X represents the functional group of a carboxylic acid or of a functional derivative thereof, for example a carboxy group of the formula —C(=O)-OH or a lower alkoxycarbonyl group of the formula —C(=O)-O-Alk in which Alk represents lower alkyl, such as methyl, but especially a halocarbonyl group of the formula —C(=O)-Hal, in which Hal represents halogen, such as chlorine or bromine, or in which X represents an amide group of the formula —C(=O)-Am, in which Am represents optionally substituted amino, for example amino, N-lower alkylamino, such as N-methylamino, or N,N-di-lower alkylamino, such as N,N-dimethyl- or N,N-diisopropyl-amino, or an orthoester group of the formula —C(O-Alk)$_3$, in which Alk represents lower alkyl, such as ethyl, or optionally with a salt thereof, under customary reaction conditions, for example in the presence of a condensing agent, such as a basic agent, and/or while heating, for example in a temperature range of from approximately 20° to approximately 200° C.

Compounds IIc in which $X_2$ is halogen, such as chlorine, or tautomers and/or salts thereof, are obtained, for example, by reacting a compound IIe in which $Y'$ and $Y''$ together represent a =N-R' group in which R' has the same meaning as in the partial structure —NHR', which represents a radical $R_1$, Y1 and $Y_4$ represent hydrogen and $Y_2$ and $Y_3$ together represent an $X_3$ group, preferably oxo, or a tautomer and/or salt thereof, with a halogenating agent, for example phosphorus oxytrichloride, it being possible for the corresponding compound IIe or a tautomer and/or salt thereof to be obtained, for example, by reaction of a compound of formula

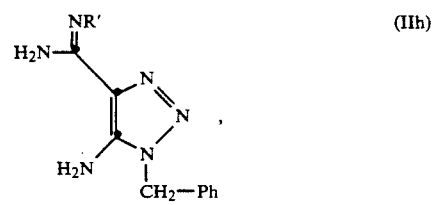

(IIh)

which in turn is obtainable from a compound IIf or a salt thereof by customary reaction with a compound of formula NH$_2$R' (IIi) or a salt thereof, or by reaction of a tautomer and/or salt thereof, with a doubled acid derivative of carbonic acid, for example urea or phosgene, under the customary reaction conditions, for example in the presence of a condensing agent, such as a basic agent, and/or while heating, for example in a temperature range of from approximately 20° to approximately 200° C.

Compounds IId, in which $X_1$ and $X_2$ are halogen, such as chlorine, or salts thereof, are obtained, for example, by reacting a compound IIe, in which $Y'$ and $Y''$ together and $Y_2$ and $Y_3$ together in each case represent oxo, and $Y_1$ and $Y_4$ each represents hydrogen, or a tautomer and/or salt thereof, with a halogenating agent, for example phosphorus oxytrichloride, and the corresponding compound IIe or a tautomer and/or salt thereof being manufactured, for example, by reacting a compound IIf or a salt thereof with a doubled acid derivative of carbonic acid, for example urea or phosgene, under customary reaction conditions.

In an especially preferred form of process, a compound IIe or a tautomer and/or salt thereof can be converted in the manner described hereinbefore into a compound IIa, IIc or IId, or into a tautomer and/or salt thereof in each case, and then, without additional purification or isolation, the resulting intermediate IIa, IIc or IId is converted in situ into a compound I or a salt thereof, the operation preferably being carried out in an aromatic hydrocarbon, for example toluene or xylene.

The compounds IIa, IIc and IId, tautomers thereof and their respective salts can also be produced in a manner analogous to that described under process variant d) by starting from a corresponding salt of formula

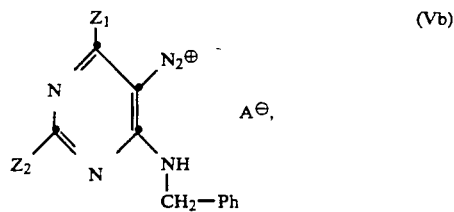

in which $Z_1$ is a nucleofugal leaving group $X_1$ and $Z_2$ is a nucleofugal leaving group $X_2$ or an $R_2$ radical, or in which $Z_1$ is an $R_1$ radical and $Z_2$ is a nucleofugal leaving group $X_2$, and in which A represents the anion of a protonic acid, and cyclising this salt Vb in a manner analogous to that described under process variant d).

What has been said hereinbefore concerning tautomers and/or salts of compounds II applies in an analogous manner to the tautomers and/or salts of the starting compounds III used in process variant b).

Optionally aliphatically substituted amino Y in compounds III, tautomers thereof and their respective salts is, for example, one of the corresponding amino groups listed hereinbefore in the definition of the radicals $R_1$ and $R_2$.

The elimination of the compound Y-H from compounds III, tautomers thereof and their respective salts is carried out in customary manner, for example in an inert solvent or diluent, for example of the kind mentioned under process variant a), by heating, for example in a temperature range of from approximately 40° to approximately 250° C., preferably from approximately 80° to approximately 200° C., and/or by treatment with an acid. Acids suitable for that purpose are, for example, mineral acids or anhydrides or acidic salts thereof, for example hydrohalic acids, sulphuric acid, alkali metal hydrogen sulphates, phosphoric acid, polyphosphoric acid, phosphorus pentoxide, phosphorus trichloride or phosphorus oxytrichloride, organic sulphonic acids, such as p-toluenesulphonic acid, or carboxylic acids or their anhydrides or halides, such as lower alkanoic acids and their anhydrides or halides, for example acetic acid, acetic anhydride or acetyl chloride, and also buffered acid solutions, for example phosphate or acetate buffers, or hydrohalides of nitrogen bases, for example ammonium or pyridinium chloride.

In a preferred form of process variant b), for example a compound III in which Y represents hydroxy, or a tautomer and/or salt thereof, is converter into a compound I or a salt thereof by heating at from 100° to 200° C. in an inert solvent, for example a lower alkanoic acid amide, such as formamide or acetamide, with the discharge of an equivalent of water.

Owing to the fact that the corresponding starting compounds III are readily available, process variant b) is especially suitable for the manufacture of compounds I in which $R_1$ is amino, or the salts thereof. Thus, starting compounds III of this kind, tautomers thereof and their respective salts can be obtained analogously to known methods and are preferably manufactured in situ, for example by cyclising a compound of formula

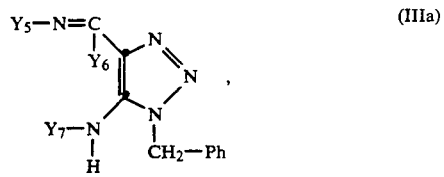

in which either $Y_5$ and $Y_7$ represent hydrogen and $Y_6$ represents a group of the formula $R_2$-C(=$X_3$)—NH- (IIIb), or $Y_5$ and $Y_6$ together represent an additional bond and $Y_7$ represents a group of the formula $R_2$-C(Y)(NH$_2$)- (IIIc), or a tautomer and/or salt thereof, the compound III or a tautomer and/or salt thereof formed as intermediate generally being further reacted in accordance with the invention without being isolated.

In groups of the formula IIIb $X_3$ represents optionally functionally modified oxo, such as oxo, thioxo, or optionally substituted imino, such as imino, N-lower alkylimino, N-cycloalkylimino or N-lower alkanoylimino, or also optionally substituted N-benzoylimino, N-lower alkanesulphonylimino or N-arylimino.

What has been said hereinbefore regarding salts and-/or tautomers of compounds II applies in an analogous manner to salts and/or tautomers of compounds IIIa.

The cyclisation of compounds IIIa, tautomers thereof, and their respective salts and optionally the subsequent in situ elimination of Y-H from the resulting compounds III or tautomers and/or salts thereof is carried out in customary manner, for example under neutral, acidic or basic conditions, if necessary in the presence of an acid or a basic agent, in the presence of an inert solvent or diluent, at room temperature or, preferably, while heating, for example in a temperature range of from approximately 20° to approximately 250° C., and/or under an inert gas, such as nitrogen. The acids, basic agents and inert solvents or diluents used may be, for example, the corresponding agents listed under process variant a). In an especially advantageous manner, however, the inert solvent or diluent may alternatively be a lower alkanoic acid amide, such as formamide or acetamide.

In an especially preferred form of process, for example a compound IIIa in which $Y_5$ and $Y_7$ represent hydrogen and $Y_6$ represents an $R_2$-C(=O)-NH- group (IIIb), or $Y_5$ and $Y_6$ together represent an additional bond and $Y_7$ represents an $R_2$-C(OH)(NH$_2$)- group (IIIc), or a tautomer and/or salt thereof, is cyclised by heating for several hours, for example in a temperature range of from approximately 80° to approximately 200° C., in a lower alkanoic acid amide, such as formamide or acetamide, and a further reaction of the resulting compound III in which Y is hydroxy, or of a tautomer and/or salt thereof, occurs in situ under the reaction conditions to yield the desired end product of formula I or a salt thereof. In an analogous manner corresponding compounds IIIa having groups IIIb in which $X_3$ is amino, or groups IIIc in which Y is amino, or tautomers and/or salts thereof, may be cyclised in an inert solvent, such as a haloalkane, for example tetrachloromethane, and further reacted to form compounds I or salts thereof.

The compounds IIIa, tautomers thereof and their respective salts are obtained from compounds of the formula

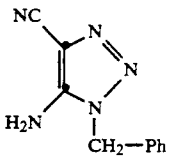
(IIId)

or salts thereof by reaction with a compound of formula $R_2$-C($=X_3$)-$NH_2$ (IIIe), in which $X_3$ represents optionally functionally modified oxo, for example of the kind described for group IIIb, or salts thereof, the operation being carried out analogously to known processes, for example at room temperature or preferably while heating, for example in a temperature range of from approximately 20° to approximately 250° C., under neutral, acidic or basic conditions, if necessary in the presence of an acid or a basic agent, for example of the kind mentioned hereinbefore, in the presence of an inert solvent or diluent, for example of the kind mentioned hereinbefore, and/or under an inert gas, such as nitrogen. The inert solvent or diluent used may be especially also a lower alkanoic acid amide, such as formamide or acetamide.

In an especially preferred form of process a compound IIId or a salt thereof is reacted with a large excess of a compound IIIe ($X_3$ represents optionally functionally modified oxo, preferably oxo), for example in formamide or acetamide ($X_3$=oxo, $R_2$=hydrogen or methyl), while heating, for example in a temperature range of from approximately 80° to approximately 200° C., to form a compound IIIa or a tautomer and/or a salt thereof, the reactant IIIe simultaneously acting as solvent or diluent.

Advantageously, though, the compounds IIIa, tautomers thereof and their respective salts are also produced in situ and further reacted, without isolation, to form compounds III or tautomers and/or salts thereof, which in turn are further reacted, in the manner described above, generally also in situ, to form compounds I or salts thereof.

Thus, in the manner of a one-pot reaction, a compound IIId or a salt thereof may be reacted, while heating, with a large excess of a compound IIIe ($X_3$ represents optionally functionally modified oxo, preferably oxo), for example in formamide or acetamide ($X_3$=oxo, $R_2$=hydrogen or methyl), during which reaction first of all a compound IIIa or a tautomer and/or salt thereof is formed, after which cyclisation to form a compound III or a tautomer and/or salt thereof occurs in situ with the application of heat being maintained, and this in turn is followed by an in-situ elimination of a compound Y-H (Y=hydroxy) to yield a compound I ($R_1$=amino, $R_2$ is, for example, hydrogen or methyl) or a salt thereof.

What has been said hereinbefore concerning tautomers and/or salts of compounds II applies in an analogous manner to the tautomers and/or salts of the starting materials IV used in process variant c).

The cyclisation of compounds IV, tautomers thereof and their respective salts to compounds I in which $R_2$ represents amino, or salts thereof, is carried out under customary cyclisation conditions, for example in a manner analogous to that described under process variant b) for the cyclisation of compounds IIIa to compounds III.

The starting materials IV, tautomers thereof and their respective salts can be obtained analogously to known methods, for example by reaction of a compound of formula

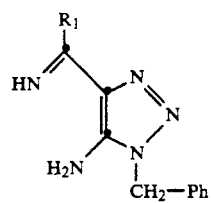
(IVa)

or a tautomer and/or salt thereof with a compound of the formula $X_1$-C$\equiv$N (IVb), in which $X_1$ represents a nucleofugal leaving group, for example of the kind described under process variant a), preferably halogen, such as chlorine or bromine, or free amino, or amino substituted as indicated for radicals $R_1$ and $R_2$, the reaction being carried out under customary reaction conditions, for example at room temperature or while heating, in an inert solvent or diluent, for example of the kind mentioned hereinbefore, optionally in the presence of a condensing agent, for example a basic agent, for example of the kind described hereinbefore, and/or under an inert gas, such as nitrogen.

What has been said hereinbefore concerning tautomers and/or salts of compounds II applies in an analogous manner to the tautomers and/or salts of the compounds IVa.

In a preferred form of process the compounds IV or tautomers and/or salts thereof are not isolated but are produced in situ and cyclised in accordance with the invention, without isolation or additional purification, to form compounds I or salts thereof.

The compounds IVa, tautomers thereof and their respective salts can be produced analogously to known methods, for example by reaction of a compound IIId or a salt thereof with ammonia or an amine of formula H-$R_1$ (IIb) or a salt thereof under customary reaction conditions.

Anions A of protonic acids in salts of formula V, which are used as starting materials according to process variant d), are, for example, anions of the acids mentioned hereinbefore for the formation of acid addition salts of compounds I, especially anions of strong inorganic protonic acids, such as anions of mineral acids, for example sulphuric acid, a phosphoric acid or a hydrohalic acid, or tetrafluoroboric acid, or anions of strong organic carboxylic acids, such as lower alkanecarboxylic acids, for example formic acid or acetic acid, for example the sulphate, phosphate, chloride, bromide, tetrafluoroborate or acetate ion.

The cyclisation of salts of formula V to compounds I or salts thereof is carried out analogously to known methods under customary reaction conditions, for example in a solvent or diluent, preferably in water, and-/or while cooling, at room temperature or while heating, for example in a temperature range of from approximately $-20°$ to approximately $+150°$ C., preferably from approximately 0° to approximately $+100°$ C.

The starting materials V are known or can be produced analogously to known methods, for example by reaction of a compound of formula

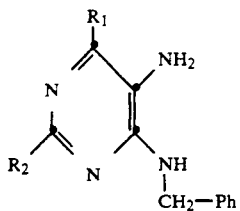

or a salt thereof with nitrous acid, the reaction being carried out under the conditions customarily used, for example in a solvent or diluent, preferably in water, and/or while cooling, at room temperature or while heating, for example in a temperature range of from approximately $-20°$ to approximately $+150°$ C. The nitrous acid is preferably produced in situ, for example by reacting an alkali metal nitrite, such as sodium nitrite, with a strong protonic acid, for example a hydrohalic acid, such as hydrochloric acid, or a lower alkanecarboxylic acid, such as formic acid or glacial acetic acid.

In an especially preferred form of process variant d), the compounds Va or salts thereof are reacted as described hereinbefore with, for example, nitrous acid that has been produced in situ, and the salts V initially formed are then, without isolation and/or additional purification, cyclised in situ in accordance with the invention to the desired compounds I or salts thereof.

The compounds Va or salts thereof are known or can be produced analogously to known methods.

Salts of the starting materials VI used in process variant e) are especially metal salts, such as alkali metal or alkaline earth metal salts, for example sodium, potassium, magnesium or calcium salts, or transition metal salts, for example pharmaceutically acceptable transition metal salts, for example zinc or copper salts, thereof.

Nucleofugal leaving groups $X_1$ in compounds VII are, for example, those of the kind indicated under process variant a).

The reaction of a compound VI with a compound VII is carried out in customary manner, for example in the presence of a basic condensing agent or, advantageously, by using the component of formula VI in the form of one of its metal salts, at room temperature or, preferably, while heating, for example in a temperature range of from approximately 20° to approximately 200° C., especially from approximately 50° to approximately 150° C., in an inert solvent or diluent, for example of the kind mentioned hereinbefore, and/or under an inert gas, such as nitrogen. Suitable basic condensing agents are especially basic condensing agents that form salts with component VI, for example the basic agents mentioned under process variant a). As mentioned, the conversion of component VI into one of its salts is especially advantageously carried out, for example, by reaction with one of the mentioned basic agents.

The starting materials VI are known or can be produced analogously to known methods, for example corresponding to process variant d) by cyclisation of corresponding salts V, which carry an unsubstituted amino group in the 4-position instead of a —NH—CH$_2$—Ph group. The starting materials VII are known or can be obtained analogously to known methods.

Compounds of formula I obtainable in accordance with the process or in some other way can be converted into different compounds of formula I by converting one or more variables of the general formula I into other variables.

For example, unsubstituted amino $R_1$ and/or $R_2$ in compounds I can be converted into N-mono- or N,N-di-lower alkylamino, and N-mono-lower alkylamino $R_1$ and/or $R_2$ can be converted into N,N-di-lower alkylamino, for example by treatment with a reactive ester of a lower alkanol, such as a lower alkyl halide, for example a lower alkyl bromide or iodide, a lower alkanesulphonate, for example methanesulphonate, an optionally substituted arylsulphonate, such as benzenesulphonate or p-toluene-sulphonate, or a di-lower alkyl sulphate, for example dimethyl sulphate, preferably under basic conditions, such as in the presence of sodium hydride or of sodium hydroxide solution or potassium hydroxide solution and advantageously in the presence of a phase transfer catalyst, such as tetrabutylammonium bromide or benzyltrimethylammonium chloride. In the course of such a conversion either only one N-lower alkyl group may be introduced, or it is possible in a single reaction step also for several, especially from 2 up to and including 4, N-lower alkyl groups to be introduced. It is also possible in successive reaction steps with suitable selection of the lower alkyl components for different N-lower alkyl groups to be introduced into unsubstituted amino or N-mono-lower alkylamino $R_1$ and/or $R_2$. According to this method of N-alkylation, in each case compounds I are obtained in which the N-lower alkyl groups introduced in the same reaction step are all the same. In analogous manner it is also possible for an N-lower alkyl group to be introduced into N-(hydroxy-lower alkyl)amino, N-monocycloalkylamino, N-mono(-cycloalkyl-lower alkyl)amino and N-lower alkanoylamino $R_1$ and/or $R_2$, resulting in N-(hydroxy-lower alkyl)-N-lower alkylamino, N-cycloalkyl-N-lower alkylamino, N-(cycloalkyl-lower alkyl)-N-lower alkylamino and N-lower alkanoyl-N-lower alkylamino $R_1$ and/or $R_2$.

Similarly, with corresponding expedient modification of the alkylation components it is also possible to convert unsubstituted amino $R_1$ and/or $R_2$ into N-(lower alkoxy-lower alkyl)amino $R_1$ and/or $R_2$ by the introduction of a N-(lower alkoxy-lower alkyl) group, into N-(hydroxy-lower alkyl)amino $R_1$ and/or $R_2$ by the introduction of a N-(hydroxy-lower alkyl) group, into N-mono- or N,N-di-cycloalkylamino $R_1$ and/or $R_2$ by the introduction of one or more, especially from 2 up to and including 4, N-cycloalkyl group(s), or into N-mono- or N,N-di-(cycloalkyl-lower alkyl)amino $R_1$ and/or $R_2$ by the introduction of one or more, especially from 2 up to and including 4, N-(cycloalkyl-lower alkyl) group(s), and also to convert N-lower alkylamino $R_1$ and/or $R_2$ into N-(hydroxy-lower alkyl)-N-lower alkylamino $R_1$ and/or $R_2$ by the introduction of a N-(hydroxy-lower alkyl) group, into N-cycloalkyl-N-lower alkylamino $R_1$ and/or $R_2$ by the introduction of a N-cycloalkyl group, or into N-(cycloalkyl-lower alkyl)-N-lower alkylamino $R_1$ and/or $R_2$ by the introduction of a N-(cycloalkyl-lower alkyl) group, and furthermore to convert N-monocycloalkylamino $R_1$ and/or $R_2$ into N,N-dicycloalkylamino $R_1$ and/or $R_2$ by the introduction of a N-cycloalkyl group as well as to convert N-mono(cycloalkyl-lower alkyl)amino $R_1$ and/or $R_2$ into N,N-di(cycloalkyl-lower alkyl)amino $R_1$ and/or $R_2$ by the introduction of a N-(cycloalkyl-lower alkyl) group.

Furthermore, unsubstituted amino $R_1$ and/or $R_2$ can be converted into N-lower alkanoylamino $R_1$ and/or $R_2$ by N-acylation, for example by reaction with a lower alkanoic acid, such as formic, acetic or propionic acid, or a reactive derivative of such an acid, for example an acid halide, such as an acid chloride, an ester or, especially, an anhydride, for example acetyl chloride or acetic anhydride. Similarly, N-lower alkylamino $R_1$ and/or $R_2$ can be converted into N-lower alkanoyl-N-lower alkylamino $R_1$ and/or $R_2$. In these conversions it is again possible either to introduce only one N-acyl group, or to N-acylate both amino or N-lower alkylamino $R_1$ and amino or N-lower alkylamino $R_2$ in one reaction step. It is also possible by suitable selection of the acylating agents to introduce different N-acyl groups into unsubstituted amino or N-lower alkylamino $R_1$ and $R_2$ in successive reaction steps. In each case compounds I are obtained in which the N-acyl groups that are introduced in the same reaction step are all the same.

Also, N-lower alkanoylamino $R_1$ and/or $R_2$ can be converted into unsubstituted amino $R_1$ and/or $R_2$, for example by reduction, that is exchange of the acyl group(s) for hydrogen, for which purpose customary reduction systems and reaction conditions are suitable, for example diborane, lithium aluminium hydride in tetrahydrofuran, diethyl ether or dioxan, sodium borohydride/cobalt(II) chloride, sodium borohydride/-trifluoro-acetic acid or trihalosilanes, such as trichlorosilane. Furthermore, N-lower alkanoylamino $R_1$ and/or $R_2$ can also be converted into unsubstituted amino $R_1$ and/or $R_2$ by hydrolysis, the hydrolysis being carried out under customary reaction conditions, for example in aqueous solution, in the presence of a basic agent, especially, for example, in the presence of an alkali metal hydroxide or lower alkanolate, such as sodium or potassium hydroxide or sodium methanolate, preferably in an organic solvent or diluent or cosolvent and/or while heating, preferably in a temperature range of from approximately 20° to approximately 150° C., especially from approximately 40° to approximately 100° C. In this process it is possible, depending on the number of equivalents of reducing agent or of basic agent used, to reduce or hydrolyse, respectively, only one or, if present, two, acyl groups(s) to unsubstituted amino $R_1$ or $R_2$, as the case may be.

Depending on the number of asymmetric carbon atoms, the novel compounds and their salts can form stereoisomers, for example diastereoisomers or enantiomers. Asymmetric carbon atoms may occur, for example in compounds I or salts thereof, in corresponding lower alkyl radicals $R_2$.

Resulting mixtures of isomers and mixtures of diastereoisomers may be separated into their components on the basis of the different physical properties thereof by customary physical separating methods, for example by distillation, crystallisation and/or chromatography.

Resulting mixtures of enantiomers, for example racemates, may be resolved according to known methods into the enantiomers, for example by recrystallisation from an optically active solvent, chromatography on chiral adsorbents, with the aid of suitable microorganisms, by cleaving with specific immobilised enzymes, by way of the formation of inclusion compounds, for example using chiral Crown ethers, in which process only one enantiomer is complexed, or by conversion into diastereoisomeric salts, for example by reaction of a basic end product racemate with an optically active acid, such as carboxylic acid, for example tartaric or malic acid, or sulphonic acid, for example camphorsulphonic acid, and separation of the diastereoisomeric mixtures obtained in this manner, for example on the basis of the different solubilities, into the diastereoisomers from which the desired enantiomer can be freed by the action of suitable agents. Advantageously, the more active stereoisomer is isolated in each case.

Further, resulting free compounds of the formula I having basic centres can be converted in a manner known per se into acid addition salts, for example by reacting a solution of the free compound in a suitable solvent or mixture of solvents with one of the aforementioned acids or with a solution thereof or with a suitable anion exchanger.

Resulting acid additions salts of compounds of the formula I can be converted in a manner known per se into the free compounds, for example by treatment with a base, such as an alkali metal hydroxide, a metal carbonate or hydrogen carbonate, or ammonia, or with a suitable anion exchanger.

Resulting acid addition salts of compounds of the formula I can be converted in a manner known per se into different acid addition salts, for example by treatment of a salt of an organic acid with a suitable metal salt, such as a sodium, barium or silver salt, of an acid in a suitable solvent in which the inorganic salt being formed is insoluble and thus separates out from the reaction mixture.

The compounds of the formula I and their salts can also be obtained in the form of their hydrates and/or may include other solvents, for example solvents optionally used for the crystallisation of substances present in solid form.

Depending on the procedure and reaction conditions, the compounds of the invention formula I may be obtained in free form or in the form of their salts.

Owing to the close relationship between the novel compounds of the formula I in free form and in the form of their salts, hereinbefore and hereinafter references to the free compounds of the formula I shall, where appropriate, also include the corresponding salts, and references to salts shall, where appropriate, also include the corresponding free compounds of the formula I.

The invention relates also to those forms of the process in which one of the compounds obtainable as intermediate at any stage of the process is used as starting material and the remaining steps are carried out, or a starting material is used in the form of a salt or, especially, is formed under the reaction conditions.

The invention relates also to novel starting materials that have been developed specifically for the manufacture of the compounds according to the invention, especially the selection of starting materials resulting in the compounds of formula I referred to at the beginning as being preferred, to processes for the manufacture thereof, and to their use as intermediates.

The invention likewise relates to the use of the compounds of formula I and the pharmaceutically acceptable salts thereof, especially as pharmacological, especially anticonvulsively effective, active substances, in which case they may be used, preferably in the form of pharmaceutical preparations, in a method for the prophylactic and/or therapeutic treatment of the animal or human body, especially as anti-convulsives, for example for the treatment of convulsions of various origins, for example for the treatment of epilepsy.

The invention relates also to pharmaceutical preparations that contain a novel compound of the formula I or a pharmaceutically acceptable salt thereof as active ingredient, and to processes for the manufacture thereof.

The invention relates also to pharmaceutical preparations that contain as active ingredient a compound of the formula I, in which Ph is a phenyl radical which is mono-substituted by halogen or by trifluoromethyl, $R_1$ is N,N-di-$C_1$-$C_6$-alkylamino in which the two N-$C_1$-$C_6$-alkyl groups may be the same or different, N-mono-$C_1$-$C_6$-alkylamino or amino, and $R_2$ is hydrogen or $C_1$-$C_6$-alkyl, in form of a pharmaceutically acceptable salt, and to processes for the manufacture thereof.

The invention relates also to pharmaceutical preparations suitable for enteral or parenteral administration that contain as active ingredient a compound of the formula I, in which Ph is a phenyl radical which is monosubstituted by halogen or by trifluoromethyl, $R_1$ is N,N-di-$C_1$-$C_6$-alkylamino in which the two N-$C_1$-$C_6$-alkyl groups may be the same or different, N-mono-$C_1$-$C_6$-alkylamino or amino, and $R_2$ is hydrogen or $C_1$-$C_6$-alkyl, in free form, and to processes for the manufacture thereof.

The pharmaceutical preparations according to the invention are preparations that contain a therapeutically effective amount of the active substance of the invention, optionally together with inorganic or organic, solid or liquid, pharmaceutically acceptable adjuncts, and that are suitable for enteral, for example oral, or parenteral administration to warm-blooded animals. Pharmaceutical preparations in dosage unit forms, such as dragées, tablets, capsules or suppositories and also ampoules, that contain the active ingredient together with diluents, for example lactose, dextrose, saccharose, mannitol, sorbitol, cellulose and/or glycine, and/or lubricants, for example silica, talc, stearic acid or salts thereof, such as magnesium or calcium stearate, and/or polyethylene glycol, are preferably used. Tablets may also contain binders, for example magnesium aluminium silicate, starches, such as corn, wheat, rice or arrowroot starch, gelatin, tragacanth, methylcellulose, sodium carboxymethylcellulose and/or polyvinyl pyrrolidone and, if desired, disintegrators, for example starches, agar, alginic acid or a salt thereof, such as sodium alginate, and/or effervescent mixtures, adsorbents, colouring substances, flavorings and/or sweeteners. Also, the active substances of the invention may be used in the form of parenterally administrable preparations or in the form of infusion solutions. Such solutions are preferably isotonic aqueous solutions or suspensions, it being possible, for example in the case of lyophilised preparations that contain the active ingredient on its own or together with a carrier, for example mannitol, to be prepared before use. The pharmaceutical preparations may be sterilised and/or may contain adjuncts, for example preservatives, stabilisers, wetting agents and/or emulsifiers, solubilisers, salts for regulating the osmotic pressure and/or buffers. The novel pharmaceutical preparations which, if desired, may contain other pharmacologically active substances, are produced in a manner known per se, for example by means of conventional mixing, granulating, confectioning, dissolving or lyophilising processes, and contain from approximately 0.1% to approximately 100%, especially from approximately 1% to approximately 50%, and in the case of lyophilisates up to 100%, active ingredient.

The dosage may depend on various factors, such as mode of administration, species of warm-blooded animal, age and/or individual condition. In the case of oral administration, the daily dose administered is normally from approximately 1 to approximately 30 mg/kg, and in the case of a warm-blooded animal weighing approximately 70 kg is preferably from approximately 0.1 g to approximately 3.0 g, and it is also possible for the daily dose to be divided for administration in several partial doses.

The following Examples serve to illustrate the above-described invention but are not intended to limit the scope thereof in any way. Temperatures are in degrees Celsius.

EXAMPLE 1

A solution of 9.22 g (35 mmol) of crude 7-chloro-3-(2-fluorobenzyl)-3H-1,2,3-triazolo[4,5-d]pyrimidine in 150 ml of toluene is added dropwise, while stirring, to a mixture of 750 ml of ethanol and 200 ml of 40% aqueous methylamine solution. The whole is left to stand for 15 hours at room temperature and then the solvent is distilled off under reduced pressure. 500 ml of water are added to the residue. The precipitated product is filtered off with suction and recrystallised from methanol. In this manner 3-(2-fluorobenzyl)-7-(N-methylamino)-3H-1,2,3-triazolo[4,5-d]pyrimidine having a melting point of 180°–182° is obtained.

The 7-chloro-3-(2-fluorobenzyl)-3H-1,2,3-triazolo-[4,5-d]pyrimidine can be obtained, for example, as follows:

70,5 g (0.3 mol) of 5-amino-1-(2-fluorobenzyl)-1H-1,2,3-triazole-4-carboxamide and 339 g (300 ml; 7.53 mol) of formamide are heated at a gentle boil for 2 hours. The reaction solution is then allowed to cool to approximately 100° and poured onto 2 l of ice-water. The precipitated product is filtered off with suction and washed with water. Drying at 100° yields 3-(2-fluorobenzyl)-3H,6H,7H-1,2,3-triazolo[4,5-d]pyrimidin-7-one having a melting point of 215°–218°.

18 g (73.5 mmol) of 3-(2-fluorobenzyl)-3H,6H,7H-1,2,3-triazolo[4,5-d]pyrimidin-7-one and 151 g (90 ml; 0.98 mol) of phosphorus oxytrichloride are heated under reflux for 4 hours and then, after having been cooled to room temperature, diluted with 1 l of toluene. Active carbon is added to the turbid solution and the whole is filtered through Hyflo. The filtrate is concentrated by evaporation under reduced pressure to approximately a quarter of its original volume. The crude 7-chloro-3-(2-fluorobenzyl)-3H-1,2,3-triazolo[4,5-d]pyrimidine can be further used in the form of the toluene solution without additional purification.

EXAMPLE 2

7-(N,N-dimethylamino)-3-(2-fluorobenzyl)-3H,1,2,3-triazolo-[4,5-d]pyrimidine is obtained in a manner analogous to that described in Example 1 starting from 7-chloro-3-(2-fluorobenzyl)-3H-1,2,3-triazolo[4,5-d]pyrimidine and using dimethylamine. It has a melting point of 117°–119° after recrystallisation from toluene/cyclohexane.

EXAMPLE 3

6.9 g (26 mmol) of 3-(2,6-difluorobenzyl)-3H,6H,7H-1,2,3-triazolo[4,5-d]pyrimidin-7-one and 50.5 g (30 ml; 327 mmol) of phosphorus oxytrichloride are heated under reflux for 1 hour. After having been cooled to room temperature, the reaction solution is diluted with 300 ml of xylene. Active carbon is added to the turbid solution and the whole is filtered through Hyflo. The filtrate is concentrated by evaporation under reduced pressure at 6° to approximately a quarter of its initial volume. This solution of crude 7-chloro-3-(2,6-difluorobenzyl)-3H-1,2,3-triazolo-[4,5-d]pyrimidine in xylene is poured into a stirred mixture of 400 ml of ethanol and 100 ml of 40% aqueous methylamine solution. After one hour, the reaction mixture is concentrated by evaporation under reduced pressure and the residue is treated with water. The precipitated crude product is filtered off with suction and recrystallised from methanol. The resulting 3-(2,6-difluorobenzyl)-7-(N-methylamino)-3H-1,2,3-triazolo[4,5-d]pyrimidine has a melting point of 225°–227°.

The 3-(2,6-difluorobenzyl)-3H,6H,7H-1,2,3-triazolo-[4,5-d]pyrimidin-7-one can be produced, for example, as follows:

7.6 g (30 mmol) of 5-amino-1-(2,6-difluorobenzyl)-1H-1,2,3-triazole-4-carboxamide and 84.7 g (75 ml; 1.88 mol) of formamide are heated under gentle reflux for 45 minutes. After having been cooled to approximately 100°, the reaction solution is poured onto 400 ml of ice-water and the precipitated product is filtered off with suction. It is washed with water and dried. The resulting 3-(2,6-difluorobenzyl)-3H,6H,7H-1,2,3-triazolo[4,5-d]pyrimidin-7-one has a melting point of 235°–237°.

EXAMPLE 4

In a manner analogous to that described in Example 3 there is obtained, starting from 3-(2-fluorobenzyl)-5-methyl-3H,6H,7H-1,2,3-triazolo[4,5-d]pyrimidin-7-one, 7-chloro-3-(2-fluorobenzyl)-5-methyl-3H-1,2,3-triazolo[4,5-d]pyrimidine and, from this, 3-(2-fluorobenzyl)-5-methyl-7-(N-methylamino)-3H-1,2,3-triazolo[4,5-d]pyrimidine having a melting point of 204°–206° (from methanol).

The 3-(2-fluorobenzyl)-5-methyl-3H,6H,7H-1,2,3-triazolo[4,5-d]pyrimidin-7-one can be obtained, for example, in a manner analogous to that described in Example 3 by heating 5.9 g (25 mmol) of 5-amino-1-(2-fluorobenzyl)-1H-1,2,3-triazole-4-carboxamide and 59 g (1 mol) of acetamide for two hours at 230°; it has a melting point of 218°–220°.

EXAMPLE 5

5 g (23 mmol) of 5-amino-4-cyano-1-(2-fluorobenzyl)-1H-1,2,3-triazole and 45 g (40 ml; 1 mol) of formamide are heated for 3 hours at 180°. The whole is cooled to room temperature and then diluted with 100 ml of water. The precipitated product is filtered off with suction and recrystallised from 75% acetic acid. The resulting 7-amino-3-(2-fluorobenzyl)-3H-1,2,3-triazolo[4,5-d]pyrimidine has a melting point of 254°–257°.

EXAMPLE 6

In a manner analogous to that described in Example 5, 7-amino-3-(2-fluorobenzyl)-5-methyl-3H-1,2,3-triazolo[4,5-d]pyrimidine having a melting point of 242°–244° is obtained by reacting 5-amino-4-cyano-1-(2-fluorobenzyl)-1H-1,2,3-triazole with acetamide.

EXAMPLE 7

It is also possible for the following to be produced in a manner analogous to that described in Examples 1 to 6:

7-(N-acetylamino)-3-(2-fluorobenzyl)-3H-1,2,3-triazolo[4,5-d]pyrimidine and 7-(N-acetyl-N-methylamino)-3-(2-fluorobenzyl)-3H-1,2,3-triazolo[4,5-d]pyrimidine.

EXAMPLE 8

There is obtained in a manner analogous to that described in Example 3, starting from 3-(2-chlorobenzyl)-3H,6H,7H-1,2,3-triazolo-[4,5-d]pyrimidin-7-one, 7-chloro-3-(2-chlorobenzyl)-3H-1,2,3-triazolo-[4,5-d]pyrimidine and, from this, by reaction with methylamine, 3-(2-chlorobenzyl)-7-(N-methylamino)-3H-1,2,3-triazolo[4,5-d]pyrimidine having a melting point of 192°–194° (from ethanol) or, by reaction with dimethylamine, 3-(2-chlorobenzyl)-7-(N,N-dimethylamino)-3H-1,2,3-triazolo[4,5-d]pyrimidine having a melting point of 131°–133° C. (from acetonitrile).

The 3-(2-chlorobenzyl)-3H,6H,7H-1,2,3-triazolo[4,5-d]pyrimidin-7-one is obtained, for example, in a manner analogous to that described in Example 3, by heating 5-amino-1-(2-chlorobenzyl)-1H-1,2,3-triazole-4-carboxamide and formamide [m.p.: 285°–288° C. (decomposition; from glacial acetic acid)].

EXAMPLE 9

There is obtained in a manner analogous to that described in Example 3, starting from 3-(2-methylbenzyl)-3H,6H,7H-1,2,3-triazolo-[4,5-d]pyrimidin-7-one, 7-chloro-3-(2-methylbenzyl)-3H-1,2,3-triazolo-[4,5-d]pyrimidine and, from this, by reaction with methylamine, 7-(N-methylamino)-3-(2-methylbenzyl)-3H-1,2,3-triazolo[4,5-d]pyrimidine having a melting point of 193°–195° (from methanol).

The 3-(2-methylbenzyl)-3H,6H,7H-1,2,3-triazolo[4,5-d]pyrimidin-7-one is obtained, for example, in a manner analogous to that described in Example 3 by heating 5-amino-1-(2-methylbenzyl)-1H-1,2,3-triazole-4-carboxamide and formamide [m.p.: 265°–267° (from glacial acetic acid)].

EXAMPLE 10

There is obtained in a manner analogous to that described in Example 3, starting from 3-(3-fluorobenzyl)-3H,6H,7H-1,2,3-triazolo[4,5-d]pyrimidin-7-one, 7-chloro-3-(3-fluorobenzyl)-3H-1,2,3-triazolo[4,5-d]pyrimidine and, from this, by reaction with methylamine, 3-(3-fluorobenzyl)-7-(N-methylamino)-3H-1,2,3-triazolo[4,5-d]pyrimidine having a melting point of 187°–189° (from toluene).

The 3-(3-fluorobenzyl)-3H,6H,7H-1,2,3-triazolo[4,5-d]pyrimidin-7-one is obtained, for example, in a manner analogous to that described in Example 3 by heating 5-amino-1-(3-fluorobenzyl)-1H-1,2,3-triazole-4-carboxamide and formamide [m.p.: 235°–237° (from 50% acetic acid)].

EXAMPLE 11

There is obtained in a manner analogous to that described in Example 3, starting from 3-(4-fluorobenzyl)-3H,6H,7H-1,2,3-triazolo[4,5-d]pyrimidin-7-one, 7-chloro-3-(4-fluorobenzyl)-3H-1,2,3-triazolo[4,5-d]pyrimidine and, from this, by reaction with methylamine, 3-(4-fluorobenzyl)-7-(N-methylamino)-3H-1,2,3-triazolo[4,5-d]pyrimidine having a melting point of 221°–223° [from ethyl acetate/ethanol (1:1)].

The 3-(4-fluorobenzyl)-3H,6H,7H-1,2,3-triazolo[4,5-d]pyrimidin-7-one is obtained, for example, in a manner analogous to that described in Example 3 by heating 5-amino-1-(4-fluorobenzyl)-1H-1,2,3-triazole-4-carboxamide and formamide [m.p.: 230°–232° (crude product)].

EXAMPLE 12

2.8 g (10 mmol) of 5-amino-7-chloro-3-(2-fluorobenzyl)-3H-1,2,3-triazolo[4,5-d]pyrimidine are dissolved in 150 ml of ethanol while heating at 40°–50°, and 10 ml of an aqueous solution of dimethylamine (40%) is added to the resulting solution. The reaction mixture is left to stand at room temperature for 2 hours. The precipitated product is then filtered off with suction and washed with water. Recrystallisation from ethanol yields 5-amino-7-(N,N-dimethylamino)-3-(2-fluorobenzyl)-3H-1,2,3-triazolo[4,5-d]pyrimidine having a melting point of 165°–167°.

The 5-amino-7-chloro-3-(2-fluorobenzyl)-3H-1,2,3-triazolo[4,5-d]pyrimidine can be produced, for example, as follows:

53 g (323 mmol) of 2-amino-4,6-dichloropyrimidine, 40.4 g (323 mmol) of 2-fluorobenzylamine and 33.4 g (330 mmol) of triethylamine are dissolved in 800 ml of ethanol and the reaction mixture is heated under reflux for 20 hours. After 400 ml of ethanol have been distilled off, the residue is diluted with 500 ml of water, and the precipitated product is filtered off with suction and recrystallised from 1 l of toluene. In this manner 2-amino-4-chloro-6-(2-fluorobenzylamino)-pyrimidine having a melting point of 130°–133° is obtained.

A solution of 11.5 g (90 mmol) of 4-chloroaniline in 33 ml of concentrated hydrochloric acid and 80 ml of water is diazotised at from 0° to 5° with a solution of 6.2 g (90 mmol) of sodium nitrite in 30 ml of water. This diazonium salt solution is then added dropwise at from 14° to 17° to a mixture of 20.6 g (81.5 mmol) of 2-amino-4-chloro-6-(2-fluorobenzylamino)-pyrimidine and 68 g (500 mmol) of crystalline sodium acetate in 500 ml of 65% acetic acid. The reaction mixture is stirred for 40 hours at room temperature, and the precipitated product is then filtered off and washed several times with water. Drying at room temperature over calcium chloride yields 2-amino-4-chloro-6-(o-fluorobenzylamino)-pyrimidine-5-azo-(4'-chlorobenzene) in the form of a yellow crystalline powder having a melting point of 215°–225° (decomposition).

59 g (151 mmol) of 2-amino-4-chloro-6-(o-fluorobenzylamino)-pyrimidine-5-azo-(4'-chlorobenzene) are suspended in 3 l of 50% ethanol and 160 ml of acetic acid and 124 g (1.9 mol) of zinc dust is introduced into the suspension in portions at 70° over a period of 1 hour under argon. The whole is stirred for a further 5 hours at 70° and then excess zinc is removed by filtration. The filtrate is concentrated in vacuo to half its volume and then rendered strongly alkaline by the addition of 240 ml of concentrated sodium hydroxide solution. The product is extracted from the mixture using ethyl acetate. After the ethyl acetate has been distilled off, the residue is recrystallised first from toluene and then from acetonitrile. In this manner 4-chloro-2,5-diamino-6-(2-fluorobenzyl-amino)-pyrimidine is obtained in the form of brown-red crystals having a melting point of 180°–182°.

A solution of 4.5 g (65 mmol) of sodium nitrite in 100 ml of water is added dropwise at 0° to a suspension of 16 g (60 mmol) of 4-chloro-2,5-diamine-6-(2-fluorobenzylamino)-pyrimidine in 200 ml of 25% acetic acid while stirring vigorously. The whole is stirred at room temperature for 2 hours and then the product is filtered off with suction. Recrystallisation from ethyl acetate/hexane yields 5-amino-7-chloro-3-(2-fluorobenzyl)-3H-1,2,3-triazolo[4,5-d]pyrimidine having a melting point of 149°–151°.

EXAMPLE 13

5-amino-3-(2-fluorobenzyl)-7-(N-methylamino)-3H-1,2,3-triazolo[4,5-d]pyrimidine having a melting point of 252°–254° (dioxan/toluene) is obtained in a manner analogous to that described in Example 12 by reacting 5-amino-7-chloro-3-(2-fluorobenzyl)-3H-1,2,3-triazolo[4,5-d]pyrimidine with methylamine.

EXAMPLE 14

There is obtained in a manner analogous to that described in Example 3, starting from 3-(3-trifluoromethylbenzyl)-3H,6H,7H-1,2,3-triazolo[4,5-d]pyrimidin-7-one, 7-chloro-3-(3-trifluoromethylbenzyl)-3H-1,2,3-triazol[4,5-d]pyrimidine and from this, by reaction with methylamine, 7-(N-methylamino)-3-(3-trifluoromethylbenzyl)-3H-1,2,3-triazolo[4,5-d]pyrimidine having a melting point of 211°–213° (from ethyl acetate) or, by reaction with dimethylamine, 7-(N,N-dimethylamino)-3-(3-trifluoromethylbenzyl)-3H-1,2,3-triazolo[4,5-d]pyrimidine having a melting point of 100°–101° (from methanol).

The 3-(3-trifluoromethylbenzyl)-3H,6H,7H-1,2,3-triazolo[4,5-d]pyrimidin-7-one is obtained, for example, in a manner analogous to that described in Example 3 by heating 5-amino-1-(3-trifluoromethylbenzyl)-1H-1,2,3-triazole-4-carboxamide and formamide (m.p.: 202°–204°).

EXAMPLE 15

A mixture of 0.82 g (10 mmol) of dimethylamine hydrochloride, 1.27 g (10 mmol) of N-cyclohexyl-N,N-dimethylamine and 1.42 g (10 mmol) of phosphorus pentoxide is heated for 15 minutes at 200°, and then 0.49 g (2 mmol) of 3-(2-fluorobenzyl)-3H,6H,7H-1,2,3-triazolo[4,5-d]pyrimidin-7-one is added to the resulting melt. The reaction mixture is maintained at 200° for 2 hours, then cooled to 100° and treated with 25 ml of water. After having been cooled to room temperature, the precipitated product is filtered off with suction, dissolved in 25 ml of ethyl acetate and the solution is dried over sodium sulphate. The ethyl acetate solution is concentrated by evaporation, the residue is recrystallised from toluene/cyclohexane and in this manner 7-(N,N-dimethylamino)-3-(2-fluorobenzyl)-3H-1,2,3-triazolo[4,5-d]pyrimidine having a melting point of 117°–119° is obtained.

The 3-(2-fluorobenzyl)-3H,6H,7H-1,2,3-triazolo[4,5-d]pyrimidin-7-one is obtained, for example, in a manner analogous to that described in Example 3 by heating 5-amino-1-(2-fluorobenzyl)-1H,1,2,3-triazole-4-carboxamide and formamide.

EXAMPLE 16

In a manner analogous to that described in Example 12, 1.95 g (6.36 mmol) of 7-chloro-5-(N,N-dimethylamino)-3-(2-fluorobenzyl)-3H-1,2,3-triazolo[4,5-d]pyrimidine are dissolved in 200 ml of warm ethanol, 7 ml of aqueous dimethylamine solution (40%) are added and the mixture is left to stand for 30 minutes. After dilution with 200 ml of water, the product is filtered off with suction and recrystallised from ethanol. In this manner 5,7-bis(N,N-dimethylamino)-3-(2-fluorobenzyl)-3H-1,2,3-triazolo[4,5-d]pyrimidine having a melting point of 123°–125° is obtained.

The 7-chloro-5-(N,N-dimethylamino)-3-(2-fluorobenzyl)-3H-1,2,3-triazolo-[4,5-d]pyrimidine can be produced, for example, as follows:

Analogously to Example 12, 13.9 g (110 mmol) of 2-fluorobenzylamine, 21.3 g (110 mmol) of 4,6-dichloro-2-(N,N-dimethylamino)-pyrimidine and 11.5 g (114 mmol) of triethylamine are dissolved in 300 ml of absolute ethanol and the mixture is heated under reflux for 48 hours. After the ethanol has been removed by distillation, water is added to the residue, the product is filtered off with suction and recrystallisation from cyclohexane yields 4-chloro-2-(N,N-dimethylamino)-6-(2-fluorobenzylamino)-pyrimidine having a melting point of 71°–73°.

4-chloro-2-(N,N-dimethylamino)-6-(o-fluorobenzylamino)-pyrimidine-5-azo-(4'-chlorobenzene) having a melting point of 175°–176° (decomposition) is obtained analogously to Example 12 from 16 g (57 mmol) of 4-chloro-2-(N,N-dimethylamino)-6-(2-fluorobenzylamino)-pyrimidine and 62 mmol of p-chlorophenyldiazonium chloride in aqueous acetic acid with 46.5 g (340 mmol) of crystalline sodium acetate.

The 4-chloro-2-(N,N-dimethylamino)-6-(o-fluorobenzylamino)-pyrimidine-5-azo-(4'-chlorobenzene) is reduced with zinc dust in ethanol/water/acetic acid analogously to Example 12 yielding 5-amino-4-chloro-2-(N,N-dimethylamino)-6-(2-fluorobenzylamino)-pyrimidine having a melting point of 103°–105° (from cyclohexane).

By reacting 6.8 g (23 mmol) of 5-amino-4-chloro-2-(N,N-dimethylamino)-6-(2-fluorobenzylamino)-pyrimidine in 150 ml of 50% acetic acid with 1.84 g (26.7 mmol) of sodium nitrite analogously to Example 12, 7-chloro-5-(N,N-dimethylamino)-3-(2-fluorobenzyl)-3H-1,2,3-triazolo[4,5-d]pyrimidine having a melting point of 153°–155° (from acetonitrile) is obtained.

EXAMPLE 17

5-(N,N-dimethylamino)-3-(2-fluorobenzyl)-7-(N-methylamino)-3H-1,2,3-triazolo[4,5-d]pyrimidine having a melting point of 199°–200° (from ethanol) is obtained in a manner analogous to that described in Example 16 using aqueous monomethylamine solution (40%).

EXAMPLE 18

It is also possible to produce the following in a manner analogous to that described in Examples 1 to 17:

7-(N-methylamino)-3-(2-trifluoromethylbenzyl)-3H-1,2,3-triazolo[4,5-d]pyrimidine, 7-(N-methylamino)-3-(4-trifluoromethylbenzyl)-3H-1,2,3-triazolo[4,5-d]pyrimidine, 3-(2-cyanobenzyl)-7-(N-methylamino)-3H-1,2,3-triazolo[4,5-d]pyrimidine, 3-(3-cyanobenzyl)-7-(N-methylamino)-3H-1,2,3-triazolo[4,5-d]pyrimidine, 3-(4-cyanobenzyl)-7-(N-methylamino)-3H-1,2,3-triazolo[4,5-d]pyrimidine, 5-amino-3-(2-chlorobenzyl)-7-(N,N-dimethylamino)-3H-1,2,3-triazolo[4,5-d]pyrimidine (melting point: 204°–206°), 7-(N,N-dimethylamino)-3-(2-fluorobenzyl)-5-(N-methylamino)-3H-1,2,3-triazolo[4,5-d]pyrimidine (melting point: 139°–140°), and 5-amino-7-(N,N-diethylamino)-3-(2-fluorobenzyl)-3H-1,2,3-triazolo[4,5-d]pyrimidine (melting point: 107°–109°).

EXAMPLE 19

Tablets each containing 50 mg of the active ingredient, for example 3-(2-fluorobenzyl)-7-(N-methylamino)-3H-1,2,3-triazolo[4,5-d]pyrimidine or a pharmaceutically acceptable salt thereof, can be produced as follows:

| Composition (for 10,000 tablets): | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch, and the mixture is moistened with an alcoholic solution of the gelatin and granulated through a sieve. After the granulate has been dried, the remainder of the potato starch, the talc, the magnesium stearate and the highly dispersed silicon dioxide are mixed in and the mixture is compressed to form tablets each weighing 145.0 mg and containing 50.0 mg of active ingredient which, if desired, may be provided with dividing notches for finer adaptation of the dose.

EXAMPLE 20

Film-coated tablets each containing 200 mg of active ingredient, for example 3-(2-fluorobenzyl)-7-(N-methylamino)-3H-1,2,3-triazolo[4,5-d]pyrimidine or a pharmaceutically acceptable salt thereof, can be produced as follows:

| Composition (for 500 tablets): | |
|---|---|
| active ingredient | 100.0 g |
| lactose | 100.0 g |
| corn starch | 70.0 g |
| talc | 8.50 g |
| calcium stearate | 1.50 g |
| hydroxypropylmethylcellulose | 1.18 g |
| shellac | 0.32 g |
| water | q.s. |
| dichloromethane | q.s. |

The active ingredient, the lactose and 40 g of the corn starch are mixed and moistened with a paste produced from 15 g of corn starch and water (while heating), and granulated. The granulate is dried, and the remainder of the corn starch, the talc and the calcium stearate are added and mixed with the granulate. The mixture is compressed into tablets (weight: 560 mg) and the tablets are film-coated with a solution of hydroxypropylmethylcellulose and the shellac in dichloromethane; final weight: 563 mg.

EXAMPLE 21

In a manner analogous to that described in Examples 19 and 20 it is also possible to produce pharmaceutical preparations containing a different compound of formula I or a pharmaceutically acceptable salt thereof, for example according to Examples 1 to 18.

I claim:

1. A pharmaceutical preparation containing an internally administrable, antiepileptically effective amount of a compound of formula

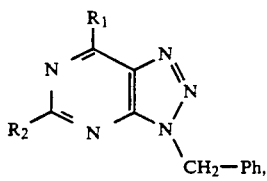 (I)

selected from the group existing of:
(a) in which Ph represents a phenyl radical that is substituted by at least one of halogen, lower alkyl, trifluoromethyl and cyano;
$R_1$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino, N-lower alkanoyl-N-lower alkylamino; and
$R_2$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino or N-lower alkanoyl-N-lower alkylamino;
(b) in which Ph represents a phenyl radical that is substituted by at least one of halogen, lower alkyl, trifluoromethyl and cyano;
$R_1$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino, N-lower alkanoyl-N-lower alkylamino; and
$R_2$ represents hydrogen or lower alkyl; in free form or in form of a pharmaceutically acceptable salt; with the proviso that, in a compound of formula I in free form, wherein $R_1$ represents N,N-di-$C_1$-$C_6$-alkylamino in which the two N-$C_1$-$C_6$-alkyl groups may be the same or different, N-mono-$C_1$-$C_6$-alkyl-amino or amino, $R_2$ is other than hydrogen and other than $C_1$-$C_6$-alkyl, if Ph represents a phenyl radical which is monosubstituted by halogen or by trifluoromethyl;
(c) a compound of formula I in free form, wherein Ph is o-fluorophenyl; $R_1$ is N-mono-methylamino or amino; and $R_2$ is hydrogen or methyl;
(d) a compound of formula I in free form, wherein Ph is o-fluorophenyl, o-chlorophenyl or m-trifluoromethylphenyl; $R_1$ is N,N-di-methylamino; and $R_2$ is hydrogen; and
(e) a compound of formula I in free form, wherein Ph is m-fluorophenyl, p-fluorophenyl, o-chlorophenyl, o-tri-fluoromethylphenyl, m-trifluoromethylphenyl or p-trifluoromehtylphenyl; $R_1$ is N-mono-methylamino; and $R_2$ is hydrogen;
or a pharmaceutically acceptable salt thereof and optionally at least one pharmaceutically acceptable adjunct.

2. A method for the treatment of epilepsy, characterized in that an antiepileptically effective amount of a compound of formula

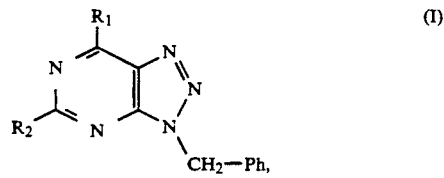 (I)

selected from the group existing of:
(a) in which Ph represents a phenyl radical that is substituted by at least one of halogen, lower alkyl, trifluoromethyl and cyano;
$R_1$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino, N-lower alkanoyl-N-lower alkylamino; and
$R_2$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino or N-lower alkanoyl-N-lower alkylamino, in free form or in form of a pharmaceutically acceptable salt;
(b) in which Ph represents a phenyl radical that is substituted by at least one of halogen, lower alkyl, trifluoromethyl and cyano;
$R_1$ represents amino, N-mono- or N,N-di-lower alkylamino, N-(lower alkoxy-lower alkyl)amino, N-(hydroxy-lower alkyl)amino, N-(hydroxy-lower alkyl)-N-lower alkylamino, N-mono- or N,N-di-cycloalkylamino, N-cycloalkyl-N-lower alkylamino, N-mono- or N,N-di-(cycloalkyl-lower alkyl)amino, N-(cycloalkyl-lower alkyl)-N-lower alkylamino, N-lower alkanoylamino, N-lower alkanoyl-N-lower alkylamino; and
$R_2$ represents hydrogen or lower alkyl; in free form or in form of a pharmaceutically acceptable salt; with the proviso that, in a compound of formula I in free form, wherein $R_1$ represents N,N-di-$C_1$-$C_6$-alkylamino in which the two N-$C_1$-$C_6$-alkyl groups may be the same or different, N-mono-$C_1$-$C_6$-alkyl-amino or amino, $R_2$ is other than hydrogen and other than $C_1$-$C_6$-alkyl, if Ph represents a phenyl radical which is monosubstituted by halogen or by trifluoromethyl;
(c) a compound of formula I in free form, wherein Ph is o-fluorophenyl; $R_1$ is N-mono-methylamino or amino; and $R_2$ is hydrogen or methyl;
(d) a compound of formula I in free form, wherein Ph is o-fluorophenyl, o-chlorophenyl or m-trifluoromethylphenyl; $R_1$ is N,N-di-methylamino; and $R_2$ is hydrogen; and
(e) a compound of formula I in free form, wherein Ph is m-fluorophenyl, p-fluorophenyl, o-chlorophenyl, o-tri-fluoromethylphenyl, m-trifluoromethylphenyl or p-trifluoromethylphenyl; $R_1$ is N-mono-methylamino; and $R_2$ is hydrogen;
or a pharmaceutically acceptable salt thereof is administered to a subject in need of such treatment.

* * * * *